US009092671B2

(12) United States Patent
Noda et al.

(10) Patent No.: US 9,092,671 B2
(45) Date of Patent: Jul. 28, 2015

(54) VISUAL LINE DETECTION DEVICE AND VISUAL LINE DETECTION METHOD

(71) Applicant: SONY CORPORATION, Tokyo (JP)

(72) Inventors: Takuro Noda, Tokyo (JP); Sayaka Watanabe, Tokyo (JP); Shinichi Haseno, Kanagawa (JP); Kenta Katagata, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/317,148

(22) Filed: Jun. 27, 2014

(65) Prior Publication Data

US 2015/0009313 A1    Jan. 8, 2015

(30) Foreign Application Priority Data

Jul. 5, 2013   (JP) .................................. 2013-141990

(51) Int. Cl.

| G03B 17/00 | (2006.01) |
|---|---|
| A61B 3/14 | (2006.01) |
| G06K 9/00 | (2006.01) |
| H04N 5/232 | (2006.01) |
| G02B 27/00 | (2006.01) |
| A61B 3/113 | (2006.01) |
| A61B 5/117 | (2006.01) |
| G02B 27/01 | (2006.01) |

(52) U.S. Cl.
CPC ............ *G06K 9/00604* (2013.01); *A61B 3/113* (2013.01); *A61B 3/14* (2013.01); *A61B 5/117* (2013.01); *G02B 27/0093* (2013.01); *G06K 9/00617* (2013.01); *H04N 5/23293* (2013.01); *G02B 27/017* (2013.01)

(58) Field of Classification Search
CPC .......... G06K 9/00604; G06K 9/00617; H04N 5/23293; G02B 27/017; G02B 27/0093; A61B 3/14; A61B 5/117
USPC ............................................. 396/51, 374, 420
See application file for complete search history.

(56) References Cited

U.S. PATENT DOCUMENTS

| 5,485,241 | A | * | 1/1996 | Irie et al. .......................... 396/51 |
|---|---|---|---|---|
| 5,583,795 | A | * | 12/1996 | Smyth ........................... 702/150 |
| 6,072,525 | A | * | 6/2000 | Kaneda .................... 348/208.15 |
| 6,424,376 | B1 | * | 7/2002 | Hirasawa ................. 348/333.03 |
| 6,426,740 | B1 | * | 7/2002 | Goto et al. ...................... 345/157 |
| 7,167,201 | B2 | * | 1/2007 | Stavely et al. ........... 348/333.03 |
| 2002/0008768 | A1 | * | 1/2002 | Takada et al. ............ 348/333.03 |

FOREIGN PATENT DOCUMENTS

JP    H05-333259 A    12/1993

* cited by examiner

*Primary Examiner* — WB Perkey
(74) *Attorney, Agent, or Firm* — Sony Corporation

(57) ABSTRACT

There is provided a visual line detection device including at least one light source configured to radiate light to an eyeball of a user observing a display surface through at least one optical member, and an imaging unit configured to acquire a captured image of the eyeball used to detect a visual line of the user on the display surface by detecting reflected light of the light from the eyeball. The reflected right from the eyeball passes through at least the optical member installed in an optical path along which the light from the display surface travels from the display surface to the eyeball of the user, and is incident on the imaging unit.

23 Claims, 17 Drawing Sheets

A-A

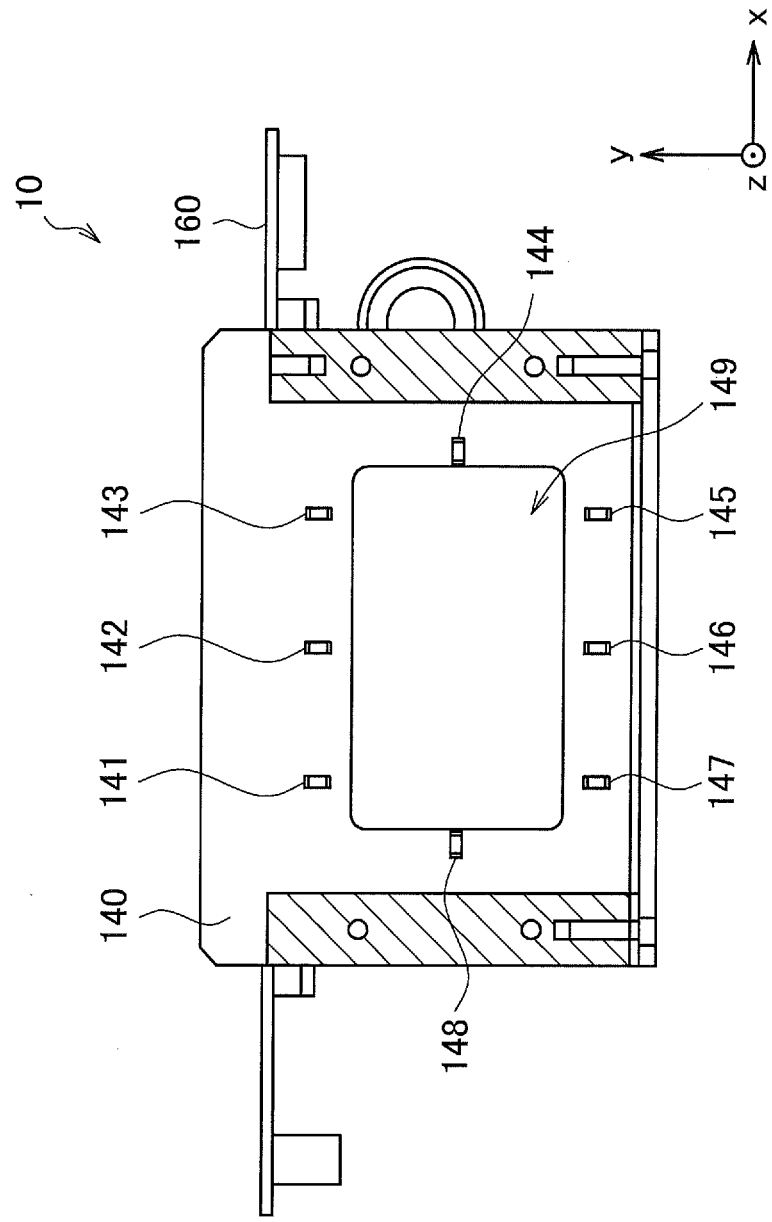

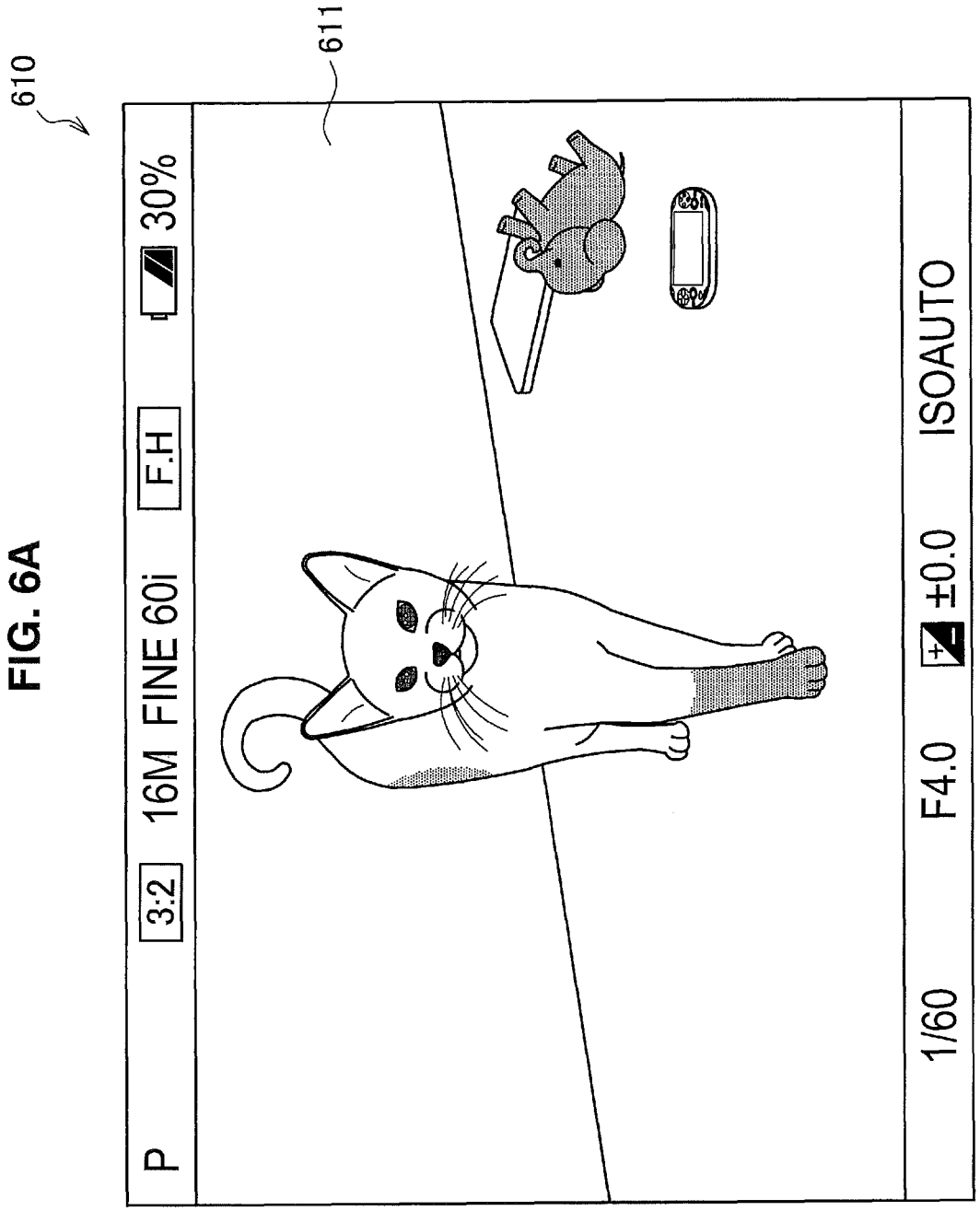

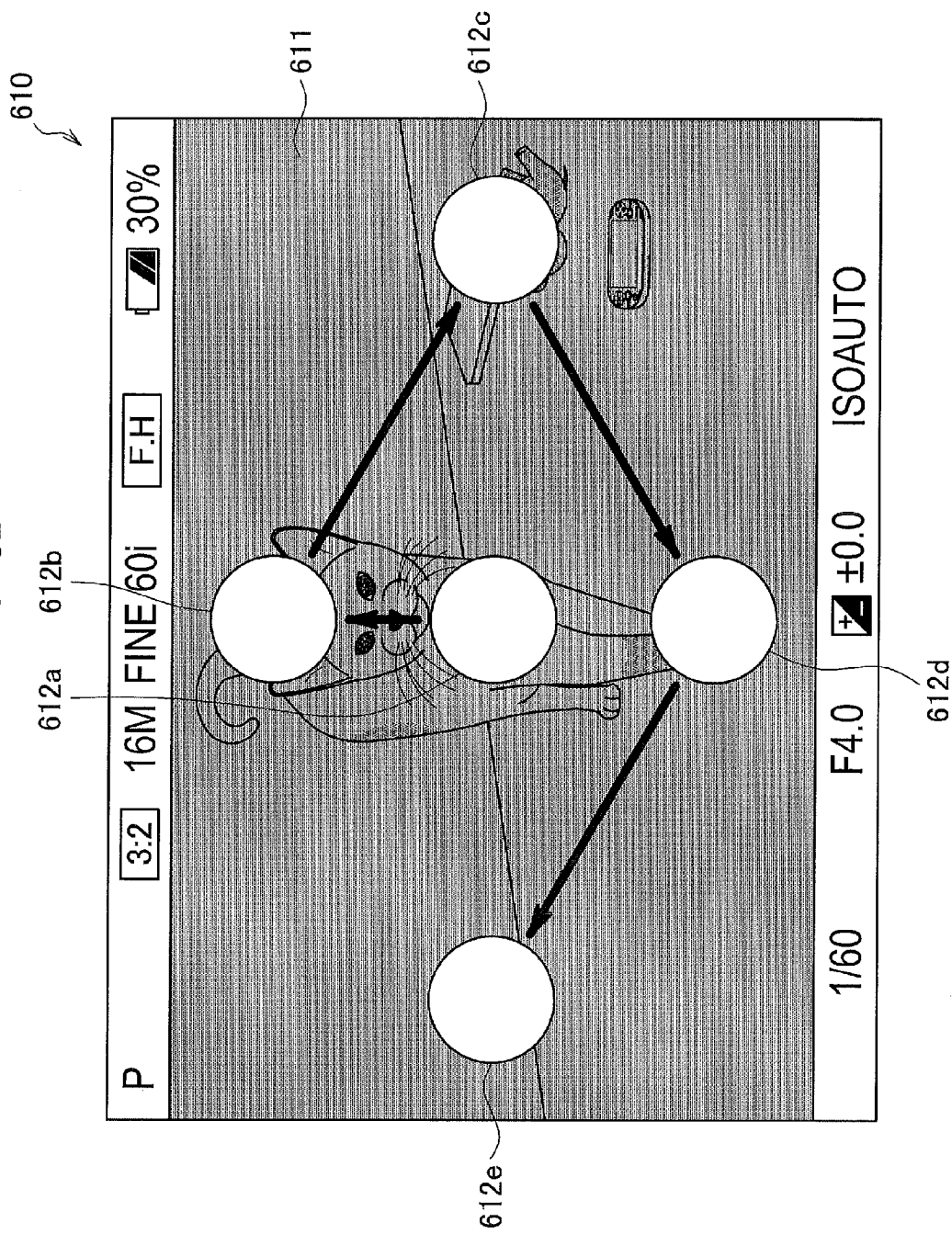

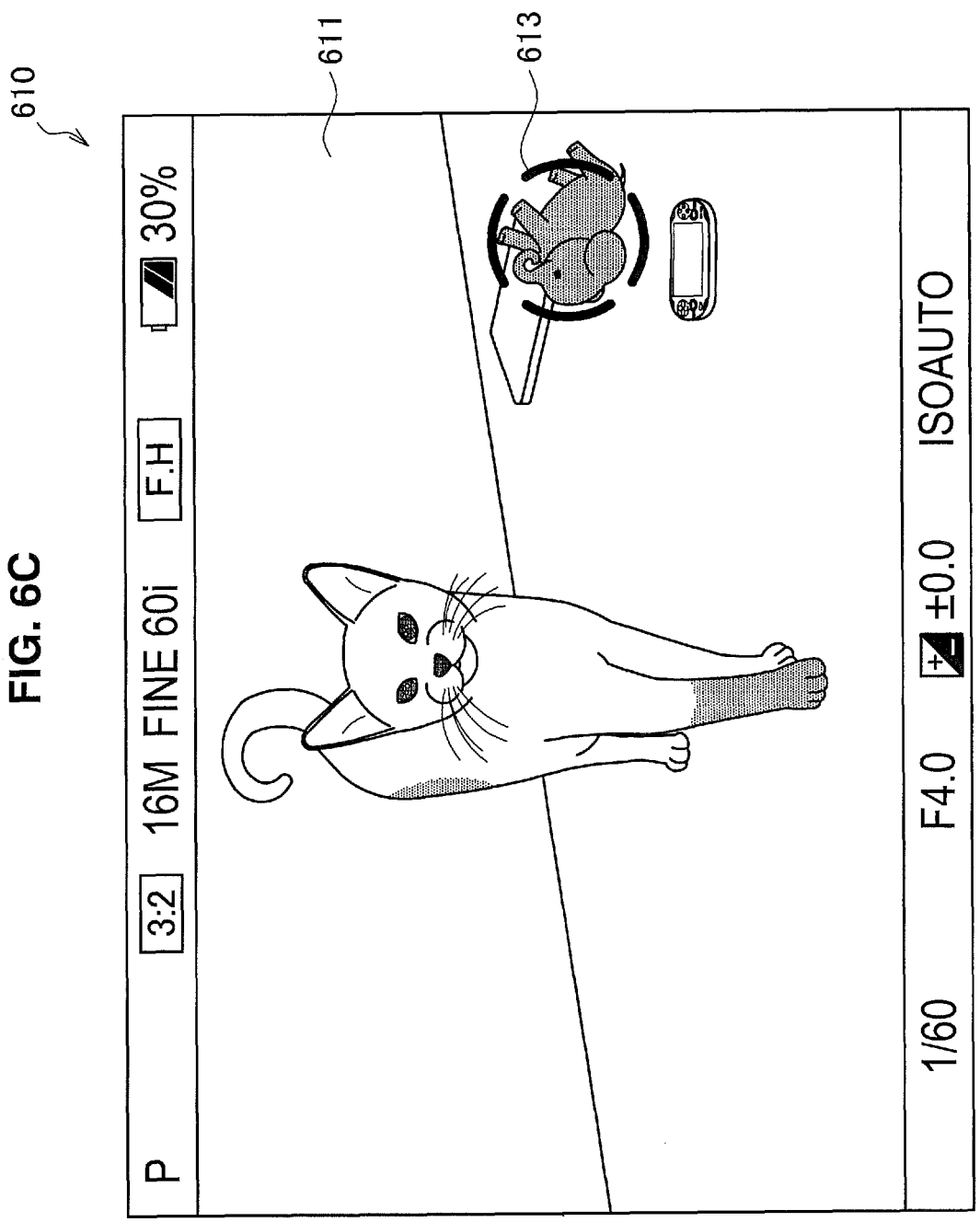

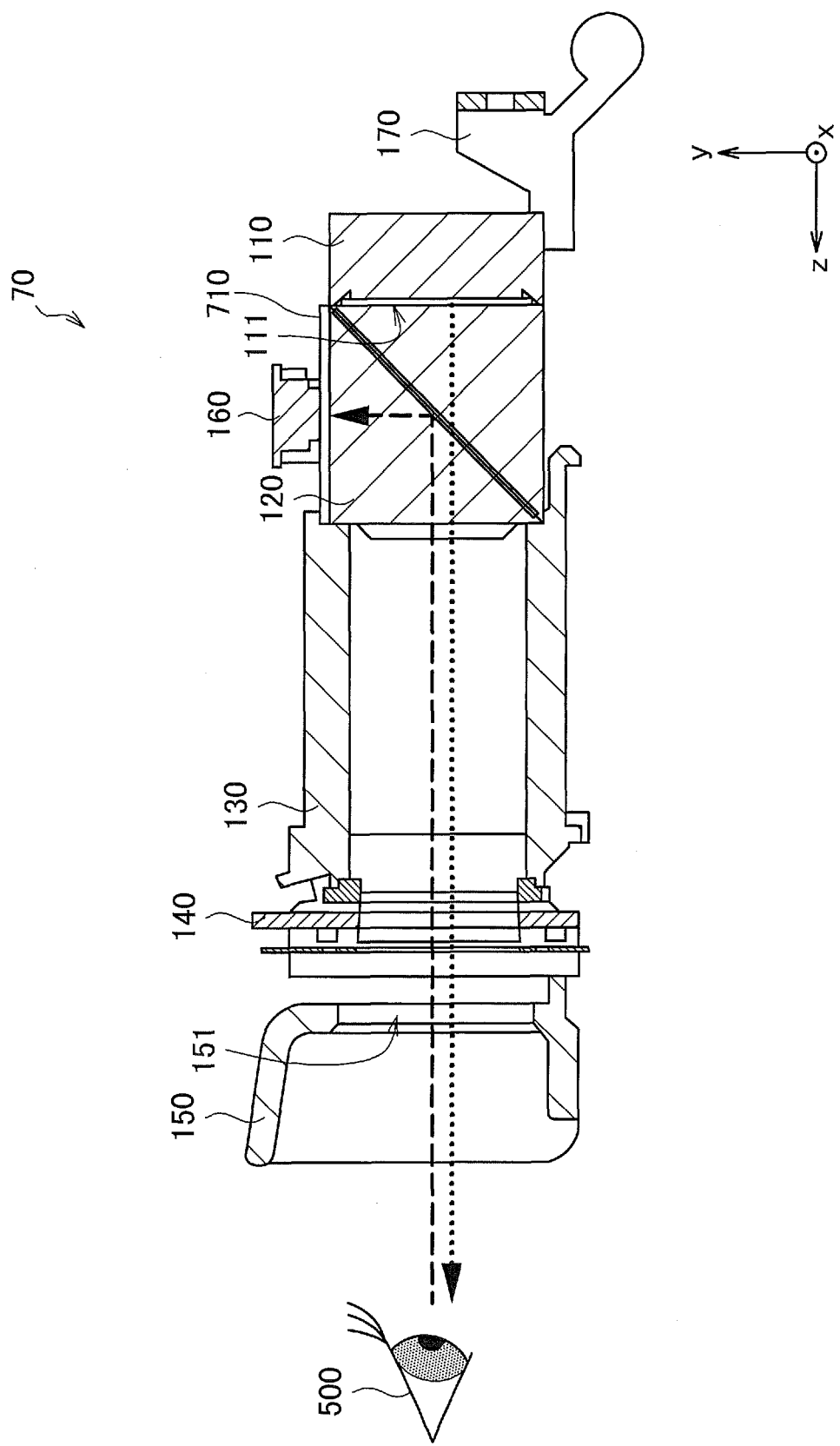

VISUAL LINE DETECTION DEVICE AND VISUAL LINE DETECTION METHOD

CROSS REFERENCE TO RELATED APPLICATIONS

This application claims the benefit of Japanese Priority Patent Application JP 2013-141990 filed Jul. 5, 2013, the entire contents of which are incorporated herein by reference.

BACKGROUND

The present disclosure relates to a visual line detection device and a visual line detection method.

Technologies for detecting visual lines of users on display surfaces on which various kinds of content are displayed and using the detected visual lines in various operations have been suggested. For example, JP H5-333259A discloses an imaging device that detects a visual line of a user on a display surface on which a through image is displayed by radiating light (infrared light) of an infrared band to an eyeball of the user looking into a finder allowing a detector to capture reflected light from the eyeball and that uses the detected visual line in auto focus (AF) adjustment.

SUMMARY

Here, in the technology disclosed in JP H5-333259A, a plurality of optical members such as prisms and lenses are installed between an eyeball of the user and the display surface on which a through image is displayed. Light from the display surface passes through the plurality of optical members and is incident on the eyeball of the user, but the reflected light from the eyeball, which is reflected light of the infrared light radiated to the eyeball of the user, follows a different optical path that does not pass the optical members and is incident on the detector. Thus, in the technology disclosed in JP H5-333259A, an optical path along which the light from the display surface on which a through image is displayed travels from the display surface to the eyeball of the user is considerably different from an optical path along which the reflected light of the radiated infrared light from the eyeball of the user travels from the eyeball to the detector. There is a concern that the considerable difference between the optical paths deteriorates precision of the detection of a visual line on the display surface.

Accordingly, it is desirable to provide a novel and improved visual line detection device and a novel and improved visual line detection method capable of further improving precision of visual line detection.

According to an embodiment of the present disclosure, there is provided a visual line detection device including at least one light source configured to radiate light to an eyeball of a user observing a display surface through at least one optical member, and an imaging unit configured to acquire a captured image of the eyeball used to detect a visual line of the user on the display surface by detecting reflected light of the light from the eyeball. The reflected right from the eyeball passes through at least the optical member installed in an optical path along which the light from the display surface travels from the display surface to the eyeball of the user, and is incident on the imaging unit.

According to an embodiment of the present disclosure, there is provided a visual line detection method including allowing light from a display surface to pass through at least one optical member and to be incident on an eyeball of a user, radiating light to the eyeball of the user observing the display surface, and acquiring a captured image of the eyeball used to detect a visual line of the user on the display surface by detecting reflected light of the light from the eyeball. The reflected light from the eyeball passes through at least the optical member installed in an optical path along which the light from the display surface travels from the display surface to the eyeball of the user, and is detected.

According to an embodiment of the present disclosure, the light from the display surface follows the first optical path that passes at least one optical member and is incident on the eyeball of the user. The reflected light from the eyeball, which is reflected light of the light radiated to the eyeball of the user, follows the second optical path, which passes at least the optical member installed in the first optical path, to be detected. Accordingly, an influence of the optical member on the light in the first optical path and an influence of the optical member on the light in the second optical path are similar. Thus, since a captured image of the eyeball is acquired based on the reflected light following the second optical path and being detected and a visual line of the user on the display surface is detected based on the captured image, the precision of the visual line detection is further improved.

According to embodiments of the present disclosure described above, it is possible to further improve the precision of the visual line detection.

BRIEF DESCRIPTION OF THE DRAWINGS

FIG. 2B is a sectional view of the visual line detection device according to the embodiment taken along the cross-section B-B illustrated in FIG. 1;

FIG. 6A is an explanatory diagram for describing a calibration process according to the embodiment;

FIG. 6B is an explanatory diagram for describing a calibration process according to the embodiment;

FIG. 6C is an explanatory diagram for describing a calibration process according to the embodiment;

FIG. 7 is a sectional view illustrating another configuration example when the visual line detection process according to the embodiment is applied to an EVF of an imaging device;

DETAILED DESCRIPTION OF THE EMBODIMENTS

Figure 1:
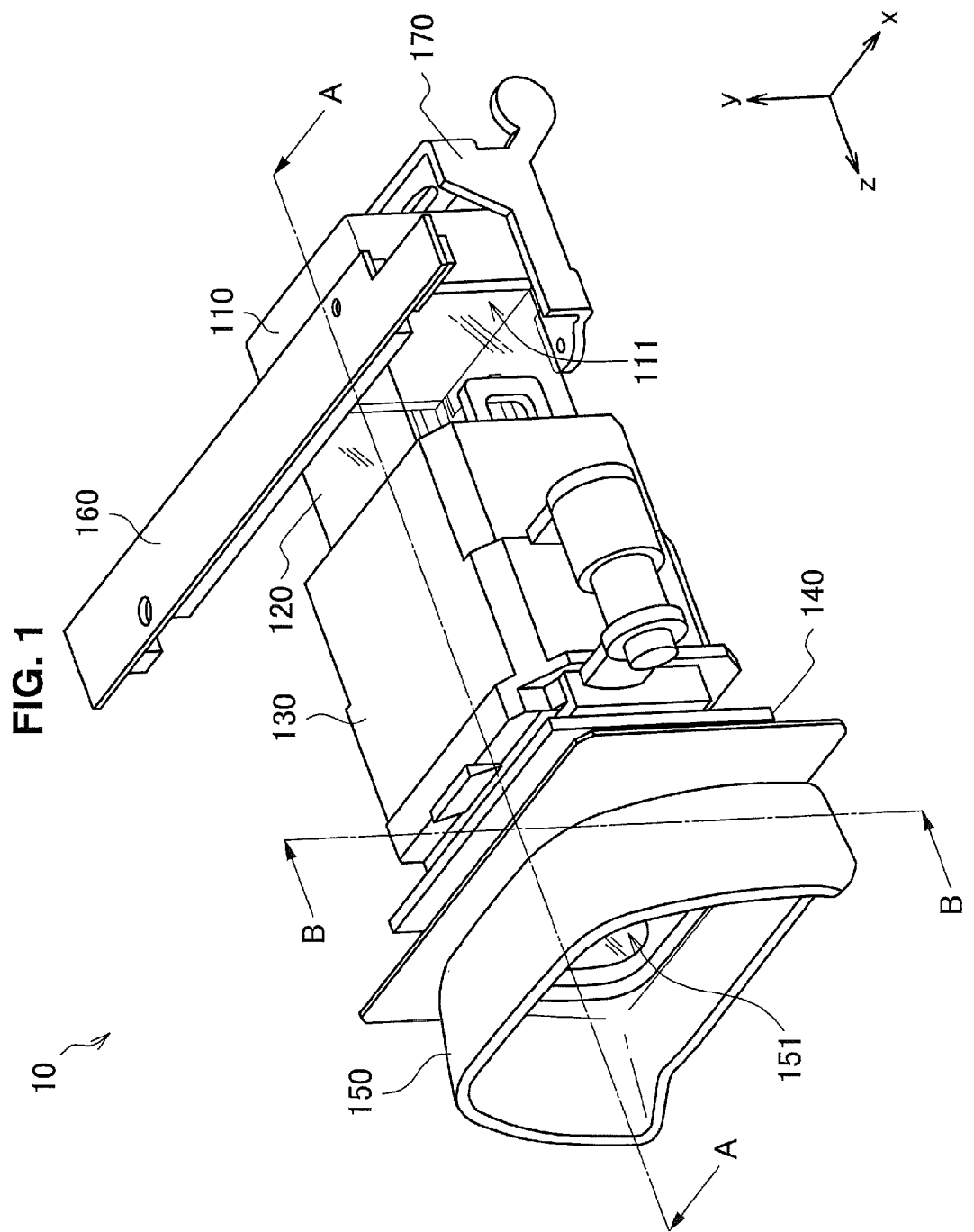
FIG. 1 is a perspective view illustrating an outer appearance and an overall configuration of a visual line detection device according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be made in the following order:
1. Outer appearance and overall configuration of visual line detection device
2. Configuration of visual line detection device
3. Details of visual line detection process
3-1. Visual line vector calculation process
3-2. Light source driving control
3-3. Calibration process
3-4. Process of reading unique user information based on iris authentication
4. Modification examples
4-1. Addition of IR filter
4-2. Application to wearable device
4-3. Application to head-mounted display
5. Processing order of visual line detection method
6. Conclusion In preferred embodiments of the present disclosure, light is radiated to an eyeball of a user observing a display surface through at least one optical member. Then, when reflected light of the radiated light from the eyeball of the user is detected, a captured image of the eyeball used to detect a visual line of the user on the display surface is acquired. Also, the reflected light of the radiated light from the eyeball of the user passes through an optical member installed in an optical path along which the light from the display surface travels from the display surface to the eyeball of the user, and is detected. In this way, the visual line of the user on the display surface is detected using the acquired captured image of the eyeball of the user. Here, observing or viewing the display surface may mean observing or viewing various kinds of content displayed on the display surface. In the following description, a series of processes including at least each of the above-described processes according to the embodiments is referred to as a visual line detection process.

Any known method may also be applied to the visual line detection process using the captured image of the eyeball of the user. In the embodiments, for example, the visual line detection process based on a pupil cornea reflection method is performed. Specifically, in the visual line detection process according to the embodiments, a pupil cornea reflection method is used to detect a visual line of a user by calculating a visual line vector indicating a direction (rotational angle) of an eyeball based on a Purkinje image and an image of a pupil contained in a captured image of an eyeball 500. However, for human beings, it is known that there is an error of an individual difference between a visual line of a user assumed based on a visual line vector of the user and a direction in which the user actually views the display surface. Accordingly, in the visual line detection process according to the embodiments, apart from the visual line vector calculation process, a calibration process is performed to acquire eyeball information regarding the eyeball 500 of the user including at least a correlation between the visual line vector and the direction in which the user views a display surface on which content is displayed. Further, the visual line of the user on the display surface is detected by performing a correction process on the calculated visual line vector based on the eyeball information. The visual line detection process according to the embodiments may include the visual line vector calculation process, the calibration process, and the correction process based on the eyeball information described above. The visual line vector calculation process, the calibration process, and the correction process based on the eyeball information will be described in detail in the following [3-1. Visual line vector calculation process] and [3-3. Calibration process].

Hereinafter, a case in which the visual line detection process according to the embodiments is applied to an electronic view finder (EVF) of an imaging device such as a digital camera will mainly be exemplified. Accordingly, in the following description, a visual line detection device according to the embodiments may mean an EVF to which the visual line detection process according to the embodiments is applied, unless otherwise mentioned. When the visual line detection process according to the embodiments is applied to an EVF, content displayed on a display surface may be, for example, a through image in which a photographing target of an imaging device to which the EVF is connected is shown. However, a device to which the visual line detection process according to the embodiments is applied is not limited to the example. The visual line detection process according to the embodiments may be applied to another device as long as the device has a display function. Specific application examples of the visual line detection process according to the embodiments to other devices will be described in detail in the following [4-2. Application to wearable device] and [4-3. Application to head-mounted display].

1. Outer Appearance and Overall Configuration of Visual Line Detection Device

Figure 2A:
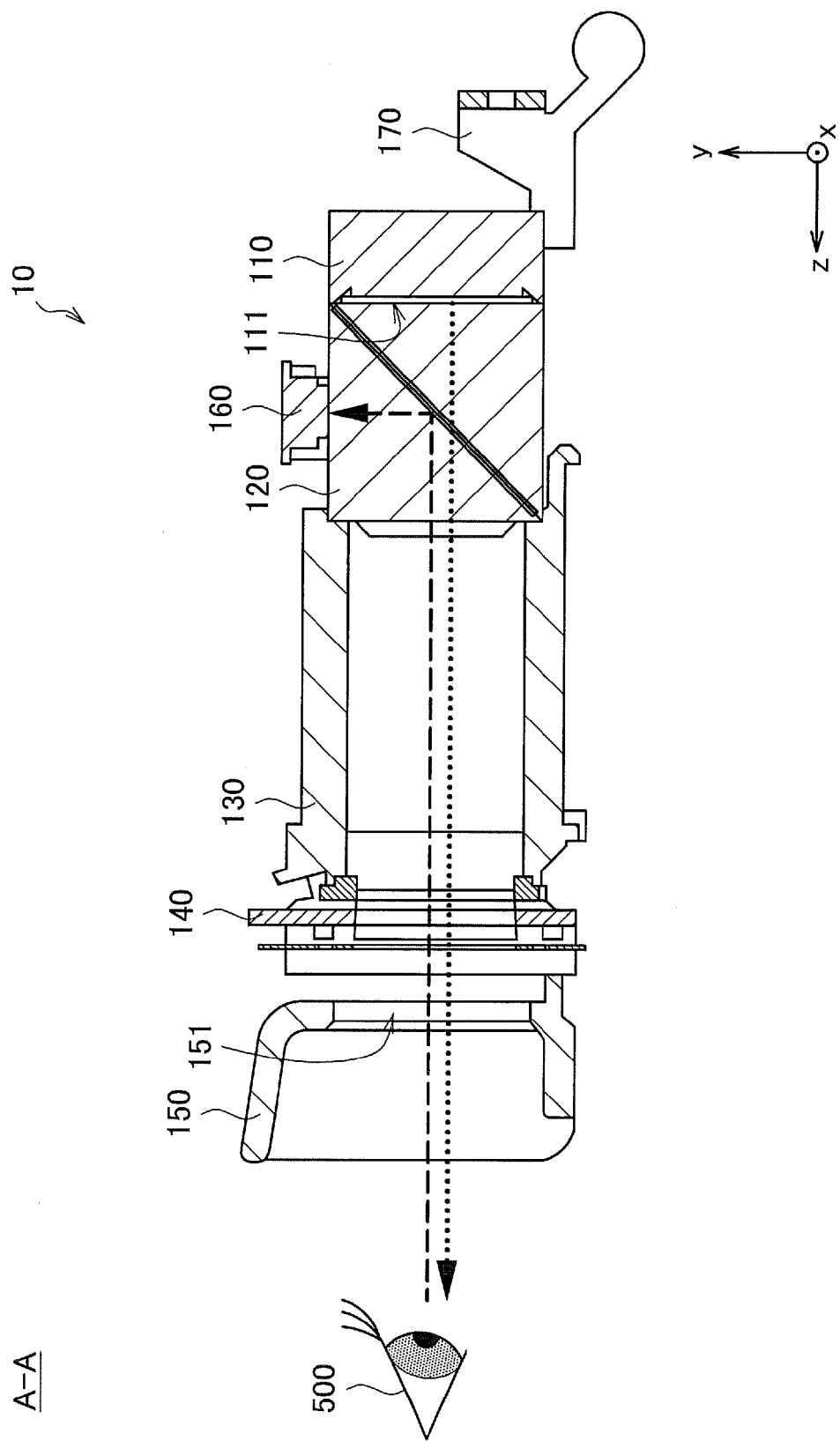
FIG. 2A is a sectional view of the visual line detection device according to the embodiment taken along the cross-section A-A illustrated in FIG. 1.

First, the outer appearance and an overall configuration of an EVF which is a visual line detection device according to an embodiment of the present disclosure will be described with reference to FIGS. 1, 2A, and 2B. FIG. 1 is a perspective view illustrating an outer appearance and an overall configuration of the visual line detection device according to an embodiment of the present disclosure. FIG. 2A is a sectional view of the visual line detection device according to the embodiment taken along the cross-section A-A illustrated in FIG. 1. FIG. 2B is a sectional view of the visual line detection device according to the embodiment taken along the cross-section B-B illustrated in FIG. 1. In FIGS. 1, 2A, and 2B, the size of each of the constituent elements of the visual line detection device is appropriately changed and illustrated, as necessary, to further clarify the description of the configuration of the visual line detection device. A magnitude relation between the constituent elements of the visual line detection device illustrated in FIGS. 1, 2A, and 2B does not necessarily precisely represent a magnitude relation between the constituent elements of an actual visual line detection device.

Referring to FIGS. 1, 2A, and 2B, a visual line detection device 10 according to an embodiment of the present disclosure includes a display unit 110, an optical path changing element 120, a magnifier unit 130, a light source substrate 140, an eyecup 150, an imaging unit 160, and a hinge 170. As illustrated in FIGS. 1 and 2A, of these constituent elements, the display unit 110, the optical path changing element 120, the magnifier unit 130, the light source substrate 140, and the eyecup 150 are arranged in one line in this order. A display surface 111 of the display unit 110 is arranged to face the optical path changing element 120. A user can observe the display surface 111 of the display unit 110 through the light source substrate 140, the magnifier unit 130, and the optical path changing element 120 from the eyecup 150. In FIG. 2A, an eyeball 500 of the user observing the display surface 111 on which content is displayed is illustrated together and a positional relation between the visual line detection device 10 and the eyeball 500 of the user is schematically illustrated. Also, the visual line detection device 10 may further include a light-shielding housing accommodating the display unit 110, the optical path changing element 120, the magnifier unit 130, the light source substrate 140, and the imaging unit 160 therein. However, in FIGS. 1, 2A, and 2B, these units are not illustrated to show the configuration of each constituent element.

Hereinafter, as illustrated in FIGS. 1, 2A, and 2B, the embodiment will be described defining a direction in which the user observes the display surface 111 of the display unit 110 from the eyecup 150 as the z-axis direction. Also, the vertical and horizontal directions at the time of viewing from the user observing the display surface 111 in a plane perpendicular to the z-axis direction, that is, a plane parallel to the display surface 111 of the display unit 110, are defined as the y-axis direction and the x-axis direction, respectively. Further, a direction oriented from the display surface 110 to the eyecup 150 is defined as the positive direction of the z axis and an upper direction when viewed by the user is defined as the positive direction of the y axis. In the following description, a position on the upstream side in the positive direction of the z axis is referred to as a "front stage" and a position on the downstream side in the positive direction of the z axis is referred to as a "rear stage" in order to express a positional relation between the constituent elements.

Here, a user observing the display surface 111 of the display unit 110 means that light from the display surface 111 passes through the optical path changing element 120, the magnifier unit 130, the light source substrate 140, and the eyecup 150 and is incident on the eyeball 500 of the user. Accordingly, the expressions "front stage" and "rear stage" described above can be said to be expressions corresponding to an optical path in which the light from the display surface 111 of the display unit 110 travels from the display surface 111 to the eyeball 500 of the user.

Hereinafter, the function and the configuration of each constituent element of the visual line detection device 10 according to the embodiment will be described in detail.

The display unit 110 is a display unit that displays various kinds of information in various forms such as images, text, and graphs on the display surface 111 to visually notify the user of the information. The various kinds of information can include various kinds of content. As illustrated in FIGS. 1 and 2A, the display unit 110 is arranged so that the display surface 111 faces in the positive direction of the z-axis. In the embodiment, the display unit 110 may be various display devices. Specifically, for example, an organic electro-luminescence display (OELD) device is used as the display unit 110. However, the embodiment is not limited to this example and any known display device such as an LED display device or a liquid crystal display device can be applied as the display unit 110.

As described above, the visual line detection device 10 according to the embodiment is an EVF and is connected to various imaging devices (not illustrated) such as digital cameras for use. In the embodiment, content displayed on the display surface 111 of the display unit 110 is a through image in the imaging device, that is, an image of a photographing target (subject) acquired by an image sensor included in the imaging device. The user can acquire a desired captured image by looking into the eyecup 150 of the visual line detection device 10 and appropriately adjusting photographing conditions (for example, an angle at which a photographing target is shown, magnification, exposure, and focus are set in the imaging device) while observing the through image displayed on the display surface 111 of the display unit 110. Also, in the through image displayed on the display surface 111 of the display unit 110, sides indicating the vertical direction on the display surface 111 may be changed by 90 degrees according to a direction in which the user observes the display surface 111. This is a process corresponding to the fact that the frame of a captured image generally has a rectangular shape and there is a probability that a direction in which the user grasps the imaging device and an angle at which the user looks into the visual line detection device 10 is rotated by 90 degrees depending on whether the user photographs the captured image so that the shorter sides of the rectangular shape are oriented in the vertical direction or the user photographs the captured image so that the longer sides of the rectangular shape are oriented in the vertical direction. For example, a sensor device configured to detect a posture (inclination) may be installed in the visual line detection device 10 or the imaging device and a direction of the display of a through image on the display surface 111 may be changed in accordance with a direction in which the user observes the display surface 111 of the display unit 110 based on the posture of the visual line detection device 10 detected by the sensor device. Also, a specific process of acquiring a through image or a captured image in the imaging device may be performed by a known function and configuration of a general imaging device. Although not illustrated in FIGS. 1, 2A, and 2B, for example, the visual line detection device 10 and the imaging device are electrically connected so that various signals used in the visual line detection process according to the embodiment, such as image signals of a through image, can be mutually transmitted and received. The transmission and reception of various signals between the visual line detection device 10 and the imaging device will be described in detail in the following 2. Configuration of Visual Line Detection Device The optical path changing element 120 is arranged on the rear stage of the display unit 110 to face the display surface 111 of the display unit 110. The optical path changing element 120 is a kind of optical member and, in the embodiment, has a function of a mirror linearly transmitting incident light in one direction and reflecting light (or a part of the light) in the other direction in a predetermined direction. Specifically, the optical path changing element 120 is, for example, a beam splitter, and transmits light incident in the negative direction of the z axis while a traveling direction of the light is maintained and reflects light incident in the positive direction of the z axis in the positive direction of the y axis. Accordingly, light from the display surface 111 of the display unit 110 is incident on the optical path changing element 120 in the negative direction of the z axis, passes inside the optical path changing element 120 in the positive direction of the z axis, and travels to the eyeball of the user. When the optical path changing element 120 is, for example, a polarization beam splitter, a polarization plate controlling a polarization direction of incident light may be appropriately installed along with the polarization beam splitter so that the above-described transmission and reflection of the incident light in a desired direction are realized.

The magnifier unit 130 is arranged on the rear stage of the optical path changing element 120. The magnifier unit 130 is a kind of optical member and, in the embodiment, has a function of expanding and displaying content on the display surface 111 of the display unit 110 for the user. Specifically, the magnifier unit 130 may be a lens system configured to include at least one of various kinds of lenses. Here, when the imaging device to which the visual line detection device 10 is connected has a size that is easy for the user to carry, the size of the visual line detection device 10 is preferably a size which does not hinder the convenience of portability for the user. Accordingly, in this case, the area of the display surface 111 of the display unit 110 in the visual line detection device 10 is assumed to have longitudinal and lateral lengths of, for example, about a few cm. Thus, when the area of the display surface 111 is relatively small, it is difficult for the user to observe even details of content displayed on the display surface 111 if the magnifier unit 130 is not installed, and thus convenience of the user observing the content may deteriorate. In the embodiment, as described above, since the magnifier unit 130 is installed between the display unit 110 and the eyeball 500 of the user and display of content on the display surface 111 is appropriately expanded to be observed by the user, the convenience of the user is improved. Also, the specific configuration of an optical member such as a lens in the magnifier unit 130 may be appropriately set so that magnification at which content displayed on the display surface 111 is easily observed by the user can be realized according to, for example, the area of the display surface 111 of the display unit 110 or a distance between the display surface 111 and the eyeball of the user (that is, the entrance of the eyecup 150).

The light source substrate 140 is arranged on the rear stage of the magnifier unit 130. The light source substrate 140 includes at least one light source on a surface (a surface located in the positive direction of the z axis) thereof. The light source radiates light toward an eyeball of the user observing the display surface 111 of the display unit 110. In the embodiment, the light source may be an LED that emits light with a wavelength band other than the visible light band, for example, light with an infrared band (hereinafter referred to as infrared light). However, the embodiment is not limited to this example and various optical elements can be applied as the light source mounted on the light source substrate 140 as long as the light sources are optical elements that emit light. Even when the light source emits light with a band other than the visible light band, such as infrared light, so that the light is radiated from the light source to an eyeball of the user, the light does not hinder the user from observing the display surface 111 of the display unit 110.

Here, the configuration of the light source 140 will be described in more detail with reference to FIG. 2B. FIG. 2B is a sectional view of the visual line detection device 10 taken along the cross section B-B illustrated in FIG. 1 and shows the shape of a cross section passing through the surface of the light source substrate 140 when viewed in the positive direction of the z axis. Referring to FIG. 2B, an opening 149 is formed in substantially the middle portion of a plate surface in the light source substrate 140. The user can observe the display surface 111 of the display unit 110 through the opening 149. The size of the opening 149 may be appropriately set in consideration of the user's visibility or the like of the display surface 111 or content displayed on the display surface 111.

In the region of the surface of the light source substrate 140 other than the opening 149, a plurality of LEDs 141 to 148 which are light sources are installed at predetermined intervals. In this way, in the embodiment, the LEDs 141 to 148 which are the plurality of light sources are arranged at positions at which light is radiated in mutually different directions with respect to an eyeball of the user. In this way, by performing a visual line detection process based on the light radiated in the mutually different directions with respect to an eyeball of the user, it is possible to improve precision of visual line direction. Advantages of the improvement in the precision of the visual line detection by radiating the light in the mutually different directions with respect to an eyeball of the user will be described in detail in the following [3-1. Visual line vector calculation process].

The plurality of LEDs 141 to 148 can be selectively driven based on predetermined driving conditions. The driving conditions may be set according to observation state information regarding states in which the user observes the display surface 111 of the display unit 110. Here, the observation state information is information unique to the user and includes, for example, at least one of information regarding the shape of an eye of the user, information regarding whether the user wears glasses, and information regarding a direction in which the user observes the display surface 111. In the embodiment, different driving conditions of the LEDs 141 to 148 may be set for each user based on such observation state information. For example, by setting the driving conditions of the LEDs 141 to 148 optimum for each user based on the observation state information and performing the visual line detection process under the driving conditions, it is possible to further improve the precision of the visual line detection.

As illustrated in FIG. 2B, in the embodiment, the plurality of LEDs 141 to 148 may be arranged so that the light is radiated to the eyeball of the user in at least vertical and horizontal directions. Specifically, in the example illustrated in FIG. 2B, the plurality of LEDs 141 to 148 are arranged to surround the circumference of the opening 149 with a substantially rectangular shape. The LEDs 141, 142, and 143 are arranged at positions corresponding to the upper side of the opening 149, the LED 144 is arranged at a position corresponding to the right side of the opening 149, the LEDs 145, 146, and 147 are arranged at positions corresponding to the lower side of the opening 149, and the LED 148 is arranged at a position corresponding to the left side of the opening 149. In this way, by arranging the LEDs 141 to 148 so that at least one LED is located on each of the right, left, upper, and lower sides of the opening 149, the light is radiated to the eyeball of the user in at least one direction of the right, left, upper, and lower sides. Accordingly, since the driving conditions of the LEDs 141 to 148 can be set in more detail, the driving conditions suitable for each user can be set. Also, the driving conditions of the LEDs 141 to 148 optimum for each user may be acquired for each user based on the precision of the detection or the like by actually performing the visual line detection process on the user while sequentially changing combinations of the LEDs 141 to 148 to be driven or the intensity of the radiated light during the visual line detection process or before the visual line detection process.

For example, driving circuits driving the LEDs 141 to 148 or a control circuit (light source driving control unit) installed, for example, in other portions of the visual line detection device 10 on the light source substrate 140 or the imaging device to which the visual line detection device 10 is connected and controlling the driving may be installed. The driving control of the LEDs 141 to 148 based on the above-described predetermined driving conditions is performed by the light source driving control unit. The driving control of the LEDs 141 to 148 will be described in detail in the following [3-2. Light source driving control].

The constituent elements of the visual line detection device 10 will be continuously described with reference to FIGS. 1, 2A, and 2B. The eyecup 150 is arranged on the rear stage of the light source substrate 140. The eyecup 150 is a member that comes in contact with an eye of the user when the user looks into the visual line detection device 10 and observes the display surface 111 of the display unit 110. The eyecup 150 has a cup shape in which an opening 151 is formed on the bottom surface and is arranged so that the opening 151 faces in the negative direction of the z axis. The user can observe the display surface 111 of the display unit 110 through the opening 151 in the direction of the cup-shaped opening of the eyecup 150. The light emitted from the LEDs 141 to 148 installed in the light source substrate 140 is radiated to the eyeball 500 of the user through the opening 151 of the eyecup 150.

In the opening 151, a lens such as an ocular lens may be appropriately installed to improve the user's visibility of the display surface 111 or prevent dust or the like from invading the inside of the visual line detection device 10. Optical characteristics of the ocular lens may be set in consideration of optical consistency with the lens system of the magnifier unit 130 installed inside the visual line detection device 10.

A sensor detecting contact with an eye of the user may be installed in the eyecup 150. Specifically, the eyecup 150 may include, for example, a contact sensor detecting contact of an object with a portion located in the positive direction of the z axis and corresponding to the edge of the cup shape so that contact of the eyecup 150 with an eye of the user can be detected by the contact sensor. For example, when the contact of the eyecup 150 with the eye of the user is detected, content may be displayed on the display surface 111 of the display unit 110. When the contact of the eyecup 150 with the eye of the user is detected, the user is assumed to be looking into the visual line detection device 10. Therefore, content may be displayed on the display unit 110 to selectively drive the display unit 110 only when the contact with the eye is detected, thereby achieving reduction in power consumption. Also, when the contact of the eyecup 150 with the eye of the user is not detected, a through image which is content may be displayed on, for example, another display unit installed in the imaging device to which the visual line detection device 10 is connected, instead of the display unit 110.

The imaging unit 160 is installed in any direction perpendicular to the z axis in the optical path changing element 120 so that a light reception surface faces the optical path changing element 120. In the example illustrated in FIGS. 1, 2A, and 2B, the imaging unit 160 is installed above the optical path changing element 120 (in the positive direction of the y axis). The imaging unit 160 is, for example, an image sensor such as a charge-coupled device (CCD) image sensor or a complementary MOS (CMOS) image sensor and acquires an image (captured image) according to incident light on the light reception surface by outputting a signal with an intensity according to an amount of light received for each pixel included in the light reception surface. Here, in the embodiment, the light is radiated from the LEDs 141 to 148 of the light source substrate 140 to the eyeball 500 of the user observing the display surface 111 of the display unit 110. Then, in reflected light of the light from the eyeball, components reflected in the negative direction of the z axis pass through the eyecup 150, the light source substrate 140, and the magnifier unit 130 in sequence and are incident on the optical path changing element 120. Here, the optical path changing element 120 has a function of reflecting the light incident in the positive direction of the z axis in the positive direction of the y axis. Accordingly, in the reflected light from the eyeball, components reflected in the negative direction of the z axis are reflected in the positive direction of the y axis by the optical path changing element 120 to arrive at the light reception surface of the imaging unit 160. In this way, in the embodiment, the light propagating through the inside of the visual line detection device 10 in the negative direction of the z axis is incident on the imaging unit 160. Accordingly, when the imaging unit 160 detects the reflected light of the light radiated from the LEDs 141 to 148 from the eyeball 500 of the user, a captured image of the eyeball 500 of the user used to detect a visual line of the user on the display surface 111 of the display unit 110 is acquired.

Any known method may be used in the visual line detection process using the captured image of the eyeball 500. In the embodiment, a visual line vector indicating a direction (rotation angle) of the eyeball is calculated using, for example, a pupil cornea reflection method based on an image of a pupil contained in the captured image of the eyeball 500 and a Purkinje image. In the visual line detection process according to the embodiment, apart from the visual line vector calculation process, a calibration process is performed to acquire eyeball information regarding the eyeball 500 of the user including at least a correlation between the visual line vector and a direction in which the user views the display surface 111. Then, the visual line of the user is detected by performing a correction process on the calculated visual line vector based on the eyeball information. To calculate the visual line vector with higher precision, the photographing conditions (for example, exposure and gain) when the imaging unit 160 images the eyeball 500 may be appropriately changed according to the intensity of the light radiated from the LEDs 141 to 148 to the eyeball 500, the characteristics of the eyeball 500, or the like. The visual line vector calculation process, the calibration process, and the correction process based on the eyeball information will be described in detail in the following [3-1. Visual line vector calculation process] and [3-3. Calibration process].

The hinge 170 is a connection member that connects the visual line detection device 10 to the imaging device. Although not illustrated in FIGS. 1 and 2A, the hinge 170 may actually be a member that connects a housing which is an outer shell of the visual line detection device 10 to the housing of the imaging device. The specific configuration of the hinge 170 is not limited to the example illustrated in FIGS. 1 and 2A. The hinge 170 may be appropriately set according to the connection shapes or the like of the housing of the visual line detection device 10 and the housing of the imaging device. In the embodiment, the visual line detection device 10 and the imaging device may be mechanically connected and the connection member is not limited to the hinge 170. The connection member may be appropriately set in consideration of a usage of the imaging device, the shapes of the housing of the visual line detection device 10 and the housing of the imaging device, or the like.

The outer appearance and the overall configuration of the visual line detection device 10 according to the embodiment of the present disclosure have been described above with reference to FIGS. 1, 2A, and 2B. In the embodiment, as described above, the display surface 111 of the display unit 110 is observed by the user through at least one optical member (for example, the optical path changing element 120 or the magnifier unit 130). Then, when the light is radiated to the eyeball 500 of the user observing the display surface 111 by the LEDs 141 to 148 which are the light sources and the reflected light of the radiated light from the eyeball 500 is detected by the imaging unit 160, a captured image of the eyeball 500 is acquired.

Here, the optical path of the light in the visual line detection device 10 according to the embodiment will be described in more detail. In the embodiment, as described above, when the user observes the display surface 111, light (that is, light forming content displayed on the display surface 111) from the display surface 111 passes through the optical path changing element 120, the magnifier unit 130, the light source substrate 140, and the eyecup 150 and is incident on the eyeball of the user. In FIG. 2A, an optical path (hereinafter also referred to as a first optical path) along which such light from the display surface 111 travels from the display surface 111 to the eyeball of the user is indicated by a dotted-line arrow. In the embodiment, on the other hand, the light (for example, infrared light) from the LEDs 141 to 148 of the light source substrate 140 is radiated to the eyeball of the user observing the display surface 111. Then, in the reflected light of the radiated light from the eyeball, components reflected in the negative direction of the z axis pass through the light source substrate 140, the magnifier unit 130, and the optical path changing element 120 in sequence, and are incident on the imaging unit 160. In FIG. 2A, an optical path (hereinafter also referred to as a second optical path) along which the reflected light from the eyeball travels from the eyeball to the imaging unit 160 is indicated by a dashed-line arrow.

When attention is paid to the dotted-line arrow and the dashed-line arrow illustrated in FIG. 2A, in the embodiment, the second optical path is configured to become an optical path including the optical members installed along the first optical path. Specifically, the second optical path is configured as an optical path passing through the optical path changing element 120 and the magnifier unit 130 (also including an ocular lens when the ocular lens is installed in the opening 151 of the eyecup 150) included in the first optical path. In this way, in the embodiment, the reflected light from the eyeball 500 passes through the optical members installed in a space in which the light from the display surface 111 travels from the display surface 111 to the eyeball of the user, and is incident on the imaging unit 160.

Here, in general, when light passes through an optical member, the characteristics of the light such as the intensity or wavelength of the light and a traveling direction are changed according to the characteristics (for example, a refractive index, a curvature, or the like when the optical member is a lens) of the optical member. Accordingly, when two different pieces of light are observed to examine a relation between the pieces of light, if optical members through which one piece of light passes are considerably different from optical member through which the other piece of light passes, that is, an optical path of the one piece of light is considerably different from an optical path of the other piece of light, it is difficult to obtain the relation between the pieces of light with high precision due to the fact that changes in characteristics by the optical members are independent from each other. Accordingly, when two different pieces of light are detected to examine a relation between the pieces of light, if the two pieces of light are allowed to pass through the same optical path as far as possible to detect the light, since the influences of the optical members on the pieces of light are the same, the relation between the pieces of light can be obtained with higher precision without relative consideration of the influences of the optical members on the light.

In the embodiment, the content displayed on the display surface 111 of the display unit 110 observed by the user can be said to be an image of which characteristics are changed due to the influences of the optical members installed in the first optical path. Likewise, a captured image of the eyeball 500 of the user acquired by the imaging unit 160 can be said to be an image of which characteristics are changed due to the influences of the optical members installed in the second optical path. In the visual line detection process, a visual line of the user on the display surface 111 is detected based on the captured image of the eyeball 500 of the user acquired by the imaging unit 160, the precision of the visual line detection can also be said to be improved as the relation between the light from the display surface 111 and the captured image of the eyeball 500 is acquired with high precision. Accordingly, as in existent general visual line detection technologies, when an optical path along which light from a display surface on which content is displayed travels from the display surface to an eyeball of the user is considerably different from an optical path along which reflected light from the eyeball of the user travels from the eyeball to a detector, there is a probability of precision of the visual line detection deteriorating due to an error caused by the different optical paths at the time of detection of a visual line of the user on the display surface. In the embodiment described above, however, the second optical path is configured to become the optical path including the optical members installed in the first optical path. Accordingly, it is possible to detect the relation between the light coming from the display surface 111 of the display unit 110 and observed by the user and the captured image of the eyeball 500 acquired by the imaging unit 160 with higher precision.

In the embodiment, by installing the light source substrate 140 on the rear stage of the magnifier unit 130, the light emitted from the LEDs 141 to 148 is radiated to the eyeball 500 of the user without reflection from the lens included in the magnifier unit 130. When an optical member such as a lens is present between the LEDs 141 to 148 and the eyeball 500 of the user, efficiency of the light radiated to the eyeball 500 deteriorates due to reflection from the optical member and components reflected by the optical member are also detected by the imaging unit 160. Thus, there is a probability of deterioration in quality (image quality) of the captured image of the eyeball 500 consequently occurring. In the embodiment, by installing the light source substrate 140 on the rear stage of the magnifier unit 130, it is possible to suppress reflection from the optical member such as a lens and acquire the captured image of the eyeball 500 with higher quality.

The visual line of the user detected through the visual line detection process according to the embodiment may be used for various operations of the imaging device connected to the visual line detection device 10. For example, the detected visual line of the user may be used for an auto focus adjustment (AF) function. Specifically, when a visual line of the user on the display surface 111 on which a through image is displayed is detected, the AF function of the imaging device may be driven to adjust focus on a region corresponding to the visual line of the user detected in the through image. Various manipulation inputs on the imaging device may also be performed according to the detected visual line of the user.

Specifically, when a visual line is detected in a predetermined region of the display surface 111, for example, a predetermined operation of switching between a photographing mode and a viewing mode of the photographed captured images or switching display of the captured image in the viewing mode may be performed.

2. Configuration of Visual Line Detection Device

Figure 3:
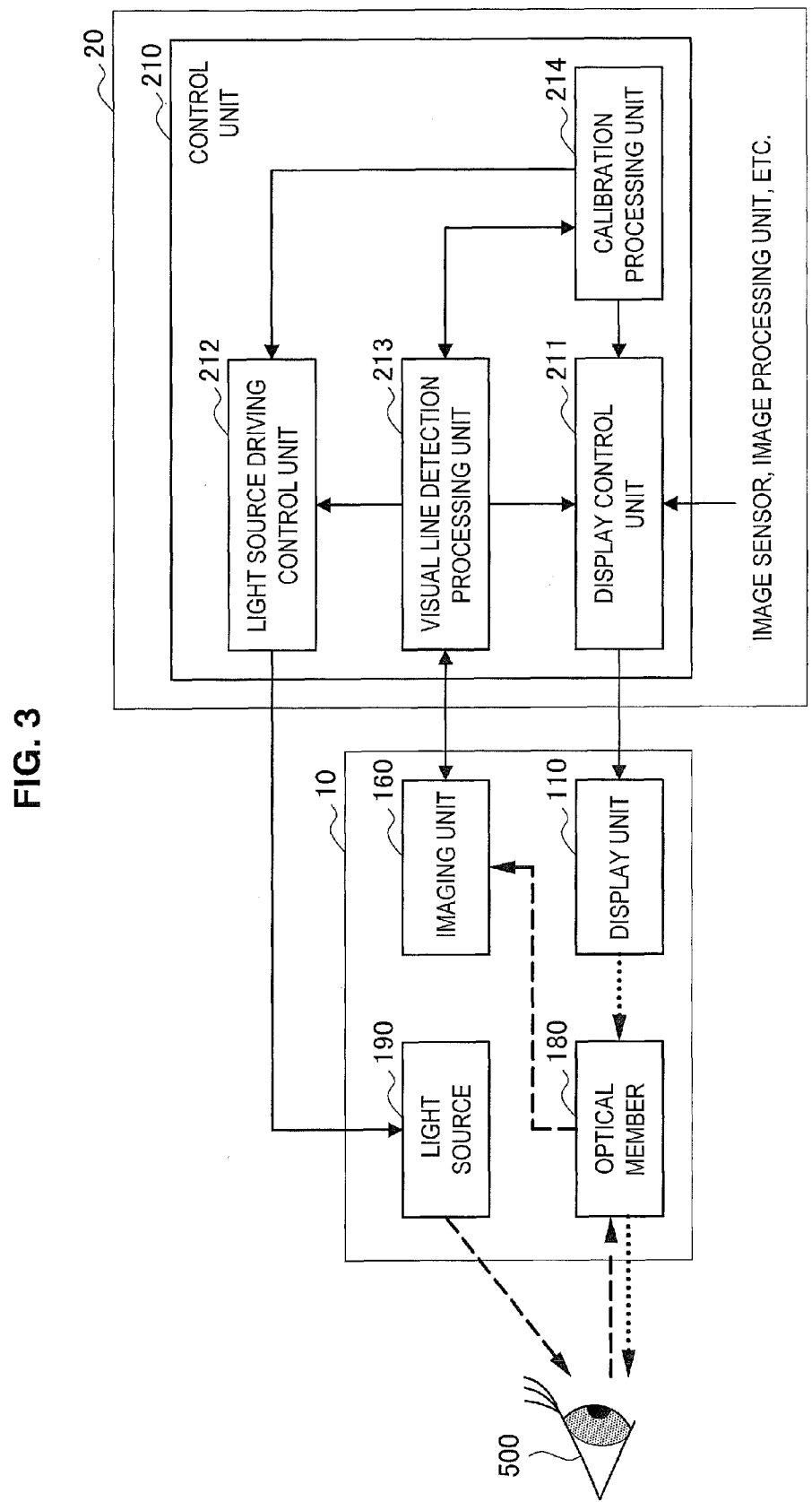
FIG. 3 is a functional block diagram illustrating an example of the configuration of the visual line detection device according to an embodiment of the present disclosure.

Next, the configuration of the visual line detection device according to an embodiment of the present disclosure will be described in more detail with reference to FIG. 3. FIG. 3 is a functional block diagram illustrating an example of the configuration of the visual line detection device according to the embodiment of the present disclosure. In FIG. 3, relations of transmission and reception of various signals and instructions between the visual line detection device 10 according to the embodiment and an imaging device 20 to which the visual line detection device 10 is connected are shown by a functional block diagram. In FIG. 3, the eyeball 500 of the user looking into the visual line detection device 10 is illustrated together to schematically show a relation between the visual line detection device 10 and the eyeball 500 of the user.

The visual line detection device 10 includes a display unit 110, an optical member 180, a light source 190, and an imaging unit 160. Here, the visual line detection device 10 illustrated in FIG. 3 has the same configuration as the visual line detection device 10 illustrated in FIGS. 1, 2A, and 2B. Specifically, the display unit 110 and the imaging unit 160 illustrated in FIG. 3 correspond to the display unit 110 and the imaging unit 160 illustrated in FIGS. 1, 2A, and 2B. The optical member 180 illustrated in FIG. 3 corresponds to the optical path changing element 120 and the magnifier unit 130 illustrated in FIGS. 1, 2A, and 2B. The light source 190 illustrated in FIG. 3 corresponds to the LEDs 141 to 148 installed in the light source substrate 140 illustrated in FIGS. 1, 2A, and 2B. The light source 190 may refer to at least one of the LEDs 141 to 148. In FIG. 3, the remaining configuration of the visual line detection device 10 described with reference to FIGS. 1, 2A, and 2B is not illustrated for simplicity.

In this way, the visual line detection device 10 illustrated in FIG. 3 corresponds to a device illustrated as the schematic functional blocks of the constituent elements of the visual line detection device 10 illustrated in FIGS. 1, 2A, and 2B. Accordingly, in FIG. 3, the detailed description of the visual line detection device 10 and the specific functions and configurations of the constituent elements of the visual line detection device 10 will be omitted.

In FIG. 3, transmission and reception of signals of various kinds of information, instructions, or the like are indicated by solid-line arrows, and exchange of light between the eyeball 500 of the user and the visual line detection device 10 and the inside of the visual line detection device 10 is schematically indicated by dotted-line arrows and dashed-line arrows. Specifically, the dotted line arrows shown in FIG. 3 schematically indicate an optical path along which light from a display surface of the display unit 110 passes through the optical member 180 and travels from the display surface to the eyeball 500 of the user. That is, an optical path indicated by the dotted-line arrows corresponds to the first optical path described in the foregoing <1. Outer appearance and overall configuration of visual line detection device>. The dashed-line arrows shown in FIG. 3 schematically indicate an optical path along which reflected light from the eyeball 500, which is reflected light of the light radiated from the light source 190 to the eyeball 500 of the user, passes from the eyeball 500 to the imaging unit 160 through the optical member 180. That is, in the optical path indicated by the dashed-line arrows, an optical path from the eyeball 500 to the imaging unit 160 corresponds to the second optical path described in the foregoing <1. Outer appearance and overall configuration of visual line detection device>. As indicated by the dotted-line arrows and the dashed-line arrows, in the embodiment, the second optical path is configured to include the optical member 180 installed in the first optical path.

The imaging device 20 is a device that has an imaging function of a digital camera or the like to which the visual line detection device 10 according to the embodiment is mechanically and electrically connected. Referring to FIG. 3, the imaging device 20 includes a control unit 210.

The control unit 210 integrally controls the visual line detection device 10 and the imaging device 20 and performs various kinds of signal processing of a visual line detection process according to the embodiment. Thus, in the embodiment, the control unit 210 installed in the imaging device 20 may perform various kinds of signal processing of the visual line detection process in the visual line detection device 10. Here, in the example illustrated in FIG. 3, in the configuration of the imaging device 20, a configuration relevant to the visual line detection process according to the embodiment is mainly illustrated and the remaining configuration is not illustrated. Accordingly, functions not directly associated with the control unit 210 and the visual line detection process according to the embodiment are not illustrated. However, the imaging device 20 may have various functions and configurations of general known imaging devices, such as an image sensor acquiring a captured image, an image processing unit performing various kinds of image processing (for example, signal processing of adjusting a black level, luminance, white balance, or the like) on the acquired captured image, and a photographing condition adjustment unit adjusting various photographing conditions (for example, exposure and a gain) when an image sensor acquires the captured image.

Hereinafter, functions and a configuration of the control unit 210 relevant to the visual line detection process according to the embodiment will mainly be described specifically with reference to FIG. 3. The control unit 210 includes a display control unit 211, a light source driving control unit 212, a visual line detection processing unit 213, and a calibration processing unit 214.

The display control unit 211 controls driving of the display unit 110 of the visual line detection device 10 and displays various kinds of information in diverse formats such as text, images, and graphs on a display screen of the display unit 110. In the embodiment, the display control unit 211 displays a through image which is an image showing a photographing target of the imaging device 20 on a display surface of the display unit 110 of the visual line detection device 10. Also, the display control unit 211 displays an image (hereinafter referred to as a calibration image) for a calibration process in the visual line detection process on the display surface of the display unit 110 according to an instruction from the visual line detection processing unit 213 and the calibration processing unit 214.

Various kinds of information regarding an image displayed on the display unit 110, such as image signals forming the through image or the calibration image, may be transmitted from an image sensor, an image processing unit, or the like installed in the imaging device 20. When the imaging device 20 includes another display unit (not illustrated), the display control unit 211 may control various kinds of display on the other display unit. Various kinds of information, such as a through image, a captured image after photographing, and a setting screen of photographing conditions, displayed on a display unit of a general known imaging device may be displayed on the other display unit.

The light source driving control unit 212 controls driving of the light source 190 such that light is radiated from the light source 190 to the eyeball 500 of the user. The light source driving control unit 212 corresponds to the driving circuit and the control circuit driving the LEDs 141 to 148 illustrated in FIG. 2B and described in the foregoing <1. Outer appearance and overall configuration of visual line detection device>. However, the driving circuit may be included in the visual line detection device 10 along with the light source 190. The light source driving control unit 212 can selectively drive the LEDs 141 to 148 which are a plurality of light sources under a predetermined driving condition. The selective driving of the LEDs 141 to 148 includes switching the LEDs 141 to 148ON and OFF or adjustment of the intensity of light emitted from each of the LEDs 141 to 148.

The driving condition under which the light source driving control unit 212 drives the LEDs 141 to 148 may be set according to observation state information regarding a state in which the user observes the display surface 111 of the display unit 110. Here, the observation state information is information unique to the user and includes, for example, at least one of information regarding the shape of an eye of the user, information regarding whether the user wears glasses, and information regarding a direction in which the user observes the display surface of the display unit 110. For example, the driving condition of the light source 190 may be set so that the visual line detection process of the user is appropriately performed according to the observation state information. A specific driving condition of the light source 190 may be instructed from the visual line detection processing unit 213 to the light source driving control unit 212. The driving control of the light source 190 by the light source driving control unit 212 will be described in detail in the following [3-2. Light source driving control].

The visual line detection processing unit 213 performs various processes relevant to the visual line detection process according to the embodiment, as well as a process of detecting a visual line of the user on the display surface of the display unit 110, based on a captured image of the eyeball 500 of the user acquired by the imaging unit 160 of the visual line detection device 10, and controls the various processes relevant to the visual line detection process. In the embodiment, in the visual line detection process, a visual line vector calculation process is performed using a so-called pupil cornea reflection method. Specifically, the visual line detection processing unit 213 calculates a visual line vector of the user indicating a direction (rotation angle) of the eyeball based on a Purkinje image and an image of a pupil contained in a captured image of the eyeball 500. Then, the visual line detection processing unit 213 detects a visual line of the user on the display surface of the display unit 110 by performing a process of correcting the calculated visual line vector based on the eyeball information of the user acquired by the calibration processing unit 214 to be described below. The eyeball information includes at least a correlation between the visual line vector of the user and a direction in which the user views the display surface. The visual line vector calculation process and the visual line vector correction process performed by the visual line detection processing unit 213 will be described in detail in the following [3-1. Visual line vector calculation process].

The visual line detection processing unit 213 may control the light to be emitted to the eyeball 500 at the time of the acquisition of the captured image of the eyeball 500 by giving an instruction of the driving condition of the light source 190 to the light source driving control unit 212. For example, the visual line detection processing unit 213 can drive the light source 190 under a predetermined driving condition by giving an instruction of the driving condition of the light source 190 set for each user to the light source driving control unit 212 according to the observation state information. In the embodiment, the driving condition of the light source 190 can be set differently for each user and the set driving condition of the light source 190 may be stored in a storage unit (not illustrated) or the like installed in the visual line detection device 10 or the imaging device 20 in association with the user. When the visual line detection device 10 is used by a user having previous experience using it, the visual line detection processing unit 213 may read the driving condition of the light source 190 corresponding to this user from the storage unit and transmit the corresponding driving condition to the light source driving control unit 212.

The visual line detection processing unit 213 may give an instruction of a photographing condition of the eyeball 500 to the imaging unit 160. An optimum photographing condition (for example, exposure or a gain) for acquiring a vivid captured image of the eyeball 500 is considered to be different according to the driving condition (for example, the positions of the LEDs 141 to 148 to be driven or the intensity of light) of the light source 190 or characteristics of the eyeball 500 (for example, a reflection ratio from the surface of the eyeball). Accordingly, to calculate the visual line vector with higher precision, the visual line detection processing unit 213 may give an instruction of the photographing condition at the time of the photographing of the eyeball 500 to the imaging unit 160 according to the driving condition of the light source 190, the characteristics of the eyeball 500, or the like. Since the photographing condition is also information unique to the user, the photographing condition may be stored in a storage unit (not illustrated) installed in the visual line detection device 10 or the imaging device 20 in association with the user. Then, as in the driving condition of the light source 190, when the visual line detection device 10 is used, the photographing condition of the imaging unit 160 according to the user may be read from the storage unit by the visual line detection processing unit 213.

The calibration processing unit 214 performs a calibration process of acquiring the eyeball information regarding the eyeball of the user used in the visual line vector correction process and controls various processes relevant to the calibration process. Since the eyeball information is information unique to the user, the calibration process is performed for each user.

In the embodiment, for example, the visual line vector calculation process is performed based on, for example, a pupil cornea reflection method, but the fact that there is an error between a visual line of the user estimated based on the visual line vector of the user and a direction in which the user actually views the display surface is known. The error is caused due to the shape or the size of the eyeball of the user and is unique to the user. In the embodiment, the eyeball information may include at least a correlation between the visual line vector and a direction in which the user views the display surface, and the visual line vector correction process is performed using the eyeball information. In this way, in the calibration process, the eyeball information regarding the eyeball of the user including at least the correlation between the visual line vector of the user and the direction in which the user views the display surface of the display unit 110 is acquired by the calibration processing unit 214.

A specific order of acquisition of the eyeball information in the calibration process will be described in brief. In the calibration process, a calibration image in which a marker is displayed on content in a superimposed manner is first displayed on the display surface of the display unit 110. Then, an action of directing a visual line toward the marker on the calibration image is performed by the user, and a visual line vector of the user who has directed his or her visual line toward the marker is calculated by the visual line detection processing unit 213. The calibration processing unit 214 can acquire a correlation between the coordinates of the marker on the display surface and the calculated visual line vector of the user as the eyeball information by receiving information regarding the visual line vector from the visual line detection processing unit 213.

The calibration processing unit 214 can perform the calibration process by transmitting and receiving various kinds of information, instructions relevant to the driving control, or the like to and from the display control unit 211 and the visual line detection processing unit 213. Specifically, the calibration processing unit 214 can give an instruction to display the calibration image on the display surface of the display unit 110 to the display control unit 211. The calibration processing unit 214 may designate the coordinates of the marker on the display surface of the display unit 110 when the calibration image is displayed. The calibration processing unit 214 can also give an instruction to perform the visual line vector calculation process to the visual line detection processing unit 213 and receive information regarding the visual line vector calculated by the visual line detection processing unit 213.

As described above, the eyeball information acquired through the calibration process is information unique to the user and is information which rarely changes for the same user when the user is an adult. Accordingly, in the embodiment, it is not necessary to perform the calibration process on the same user a plurality of times. The acquired eyeball information may be stored in a storage unit (not illustrated) installed in the visual line detection device 10 or the imaging device 20 in association with the user. When the visual line detection device 10 is used by a user having previous experience using it, a process of reading data of a parameter corresponding to the user from the storage unit may be performed instead of the calibration process. When the process of storing the eyeball information and the process of reading the eyeball information are performed, the calibration process may be performed only for a new user, and therefore convenience for the user is improved.

The overall configuration of the visual line detection device 10 according to the embodiment has been described in detail with reference to FIG. 3 together with the exchange of information with the imaging device 20 to which the visual line detection device 10 is connected.

In the embodiment, as described above, the second optical path includes the optical member 180 included in the first optical path. That is, the reflected light from the eyeball 500 passes through the optical member included in the first optical path and is incident on the imaging unit 160. Then, the visual line detection process is performed on the display surface of the display unit 110 by the visual line detection processing unit 213 based on the light following the second optical path and incident on the imaging unit 160. Accordingly, it is possible to further improve the precision of the visual line detection on the display surface.

In the embodiment, as described above, the driving condition of the light source 190 based on the observation state information and the information unique to the user, such as the eyeball information, may be stored in a storage unit or the like in association with the user. The driving condition or the eyeball information may be read and may be used in the visual line detection process, as necessary. To realize the process of storing the driving condition and the eyeball information and the process of reading the driving condition and the eyeball information, the visual line detection device 10 or the imaging device 20 may have a function of registering a user or a function of selecting a registered user. Instead of the function of selecting a user, the visual line detection device 10 or the imaging device 20 may have various personal authentication functions or individual identification functions so that a user can automatically be recognized. As the personal authentication or individual identification, for example, various kinds of biometric authentication such as fingerprint authentication, vein authentication, and iris authentication based on the captured image of the eyeball 500 of the user captured by the imaging unit 160 can be applied. For example, when the visual line detection device 10 is used, a process of selecting one user among a plurality of users registered in advance, a personal authentication process of the user, or an individual identification process of the user is performed so that the process of reading the driving condition and the eyeball information corresponding to the selected or recognized user can automatically be performed. The control unit 210 may have a function of controlling each constituent element or various information processing functions to perform the above-described personal authentication process or individual identification process, the process of reading the information unique to the user, or the like.

The case in which the control unit 210 installed in the imaging device 20 controls various processes in the imaging device 20 and controls various processes in the visual line detection device 10 including the visual line detection process has been described above, but the embodiment is not limited to this example. In the embodiment, the functions of the control unit 210 may be arbitrarily divided into a plurality of units, which may be installed in a plurality of respective devices. For example, the visual line detection device 10 may include a separate control unit and the control unit may control various processes of the visual line detection process according to the embodiment. Thus, in the embodiment, the visual line detection device 10 and the imaging device 20 may each include the control unit, and various processes in each device may be controlled by the control unit installed in each device. For example, the visual line detection device 10 and the imaging device 20 may be connected to another device (for example, an information processing device such as a PC or a server) in a wired or wireless manner to communicate with the other device, and various process of the visual line detection process according to the embodiment may be controlled by a control unit installed in the other device. In the embodiment, as exemplified above, various processes of the above-described visual line detection process may be performed and the specific configuration for realizing the visual line detection process is not limited to the configuration exemplified in FIG. 3. For example, the visual line detection device 10 and the imaging device 20 may be configured integrally as one device. The control unit 210, the separate control unit installed in the above-described visual line detection device 10, and the control unit installed in the other device can be configured by, for example, various processing circuits such as a central processing unit (CPU), a digital signal processor (DSP), or a microcomputer (microcontroller).

3. Details of Visual Line Detection Process

Next, the details of the visual line detection process according to the embodiment will be described. Hereinafter, the visual line vector calculation process performed by the above-described visual line detection processing unit 213 will first be described in [3-1. Visual line vector calculation process]. Subsequently, the driving control of the light source based on the predetermined driving control at the time of acquisition of the captured image of the eyeball of the user in the visual line vector calculation process will be described in [3-2. Light source driving control]. Further, the calibration process performed by the calibration processing unit 214 will be described in [3-3. Calibration process]. Finally, the iris authentication at the time of reading the information unique to the user, such as a result of the calibration process, will be described in [3-4. Process of reading unique user information based on iris authentication].

[3-1. Visual Line Vector Calculation Process]

Figure 4:
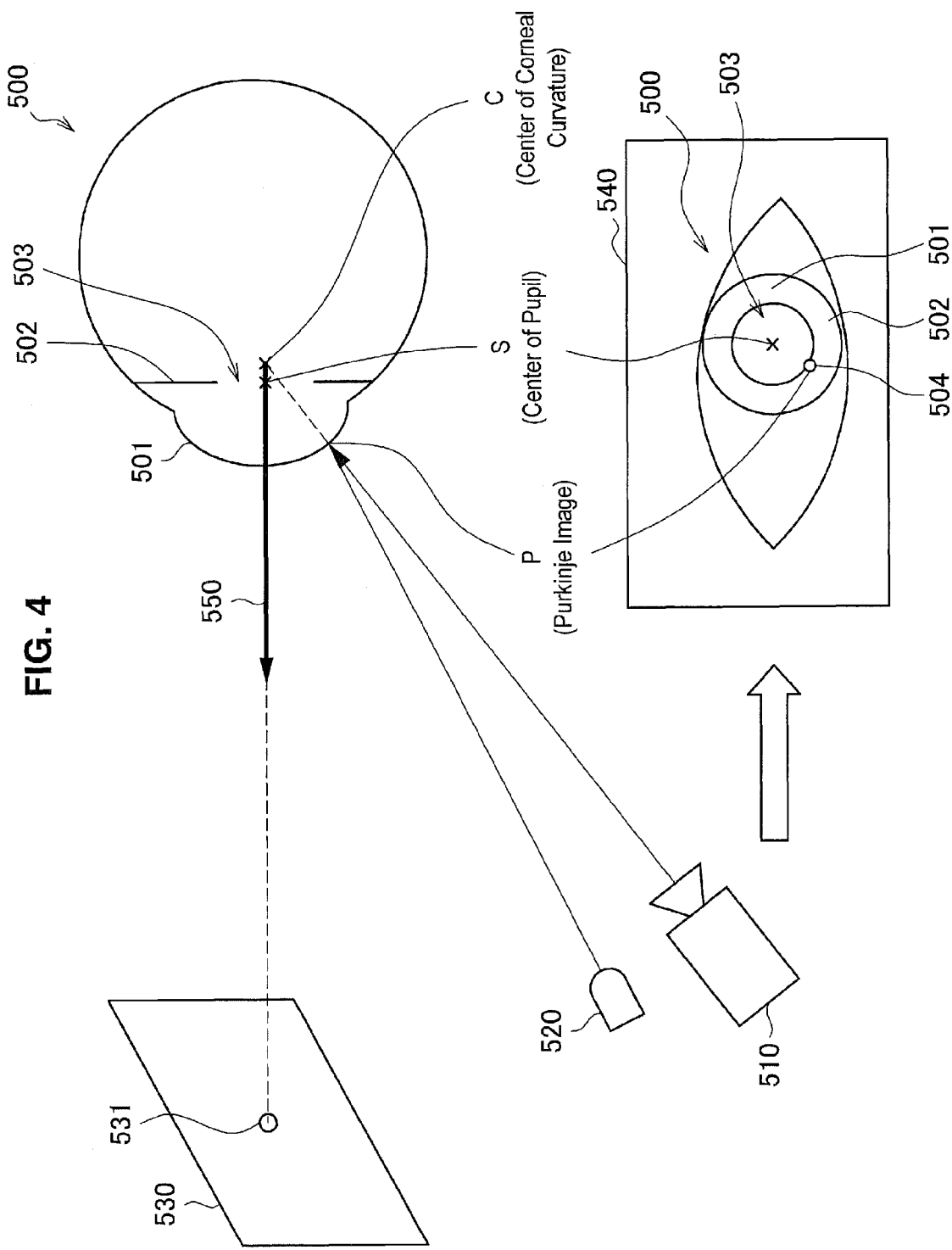
FIG. 4 is an explanatory diagram illustrating a visual line vector calculation process using a pupil cornea reflection method according to the embodiment.

First, the visual line vector calculation process performed by the visual line detection processing unit 213 will be described with reference to FIG. 4. As described above, a pupil cornea reflection method is used in the visual line vector calculation process according to the embodiment. FIG. 4 is an explanatory diagram illustrating the visual line vector calculation process using the pupil cornea reflection method according to the embodiment.

FIG. 4 illustrates a case in which light is radiated from a light source 520 to an eyeball 500 of the user observing a display surface 530, and the eyeball 500 is photographed by an imaging unit 510.

In FIG. 4, a cornea 501, an iris 502, and a pupil 503 are schematically shown in the configuration of the eyeball 500. The eyeball 500 corresponds to the eyeball 500 illustrated in FIGS. 2A and 3. The eyeball of the user looking into the visual line detection device 10 according to the embodiment is shown. The display surface 530 corresponds to the display surface 111 of the display unit 110 shown in FIGS. 1, 2A, and 3. Content, e.g., a through image in the imaging device 200, is displayed on the display surface 530. The user is observing the display surface 530 on which the content is displayed and a visual line of the user, that is, a direction of the eyeball 500, faces to a predetermined region on the display surface 530.

As described in the foregoing <2. Configuration of visual line detection device>, a visual line of the user is detected by calculating a visual line vector indicating a direction (rotation angle) of the eyeball based on a Purkinje image and an image of a pupil contained in a captured image of the eyeball 500 in the pupil cornea reflection method. To calculate the visual line vector, light is first radiated from the light source 520 to the eyeball 500 of the user observing the display surface 530. The light source 520 schematically indicates one of the LEDs 141 to 148 illustrated in FIG. 2B. In FIG. 4, an optical path of the light radiated from the light source 520 is schematically indicated by an arrow.

Subsequently, when the imaging unit 510 detects the reflected light from the eyeball 500, which is reflected light of the light radiated from the light source 520 to the eyeball 500, a captured image of the eyeball 500 is photographed. The imaging unit 510 corresponds to the imaging unit 160 illustrated in FIGS. 1, 2A, and 3. In FIG. 4, an example of the captured image photographed by the imaging unit 510 is illustrated as a captured image 540. In the example illustrated in FIG. 4, the captured image 540 is a captured image photographed when the eyes of the user face substantially the front side and the cornea 501, the iris 502, and the pupil 503 of the eyeball 500 are photographed. A Purkinje image 504 which is a light spot of the radiated light radiated from the light source 520 to the eyeball 500 is photographed in the captured image 540.

Subsequently, the visual line vector calculation process is performed based on the captured image 540. First, an image of the pupil 503 is detected from the captured image 540. In the process of detecting the image of the pupil 503, general known image recognition technologies can be applied. For example, in the process of detecting the image of the pupil 503, a series of processes such as various kinds of image processing (for example, processes of adjusting distortion, a black level, white balance, and the like) on the captured image 540, a process of acquiring a luminance distribution in the captured image 540, a process of detecting the contour (edge) of the image of the pupil 503 based on the luminance distribution, and a process of approximating the detected contour of the image of the pupil 503 to a figure such as a circle or an ellipse may be performed.

Subsequently, the Purkinje image 504 is detected from the captured image 540. In the process of detecting the Purkinje image 504, general known image recognition technologies, as in a process of detecting a center of a pupil S can be applied. For example, in the process of detecting the Purkinje image 504, a series of processes such as various kinds of image processing on the captured image 540, a process of acquiring a luminance distribution in the captured image 540, and a process of detecting pixels with luminance values considerably different from those of neighboring pixels may be performed based on the luminance distribution. A Purkinje point P indicating a point of the center of the Purkinje image 504 is also detected from the detected Purkinje image 504.

Subsequently, 3-dimensional coordinates of the center of the pupil S and the center of corneal curvature C (a center of a sphere when the cornea 501 is regarded as a part of the sphere) of the cornea 501 are calculated. The 3-dimensional coordinates of the center of the pupil S are calculated based on the image of the pupil 503 detected from the captured image 540. Specifically, 3-dimensional coordinates of the center of the pupil S are calculated by calculating 3-dimensional coordinates of each point on the contour of the image of the pupil 503 in the captured image 540 based on parameters such as a positional relation between the imaging unit 510 and the eyeball 500, light refraction on the surface of the cornea 501, and a distance between the center of corneal curvature C of the cornea 501 and the center of the pupil S and obtaining the center of the coordinates. The center of corneal curvature C of the cornea 501 is calculated based on the Purkinje image 504 detected from the captured image 540 and the Purkinje point P. Specifically, the 3-dimensional coordinates of the center of corneal curvature C of the cornea 501 is calculated by calculating the coordinates of a point advanced by a radius of curvature (a radius of curvature of a sphere when the cornea 501 is regarded as a part of the sphere) of the cornea 501 from the surface of the cornea 501 on an extension line of a straight line connecting the imaging unit 510 and the Purkinje point P inside the eyeball 500 based on parameters such as a positional relation among the imaging unit 510, the light source 520, and the eyeball 500 and the radius of curvature of the cornea 501. Since a known method used in a general pupil cornea reflection method can be applied to the process of calculating the 3-dimensional coordinates of the center of the pupil S and the center of corneal curvature C of the cornea 501 according to the embodiment, the detailed description will be omitted.

Subsequently, a visual line vector 550 is calculated by calculating a vector oriented from the center of corneal curvature C of the cornea 501 to the center of the pupil S. By acquiring a positional relation between the display surface 530 and the eyeball 500 in advance, the coordinates of a region 531 in which an extension line of the visual line vector 550 and the display surface 530 intersect can be obtained. Therefore, the region 531 is a region indicating the visual line of the user on the display surface 530.

The visual line detection processing unit 213 illustrated in FIG. 3 and described in the foregoing <2. Configuration of visual line detection device> can calculate the visual line vector 550 indicating a direction of the eyeball 500 of the user by performing each of the above-described processes and detect the coordinates of the region (that is, the coordinates of the region 531 illustrated in FIG. 4 on the display surface 530) corresponding to the visual line vector 550 on the display surface 530 (that is, the display surface of the display unit 110 illustrated in FIG. 3).

However, for human beings, it is known that a direction in which an eyeball faces (that is, a direction indicated by the visual line vector 550) does not necessarily accord with a direction in which a human being actually views in a visual line. This is caused due to the shape or size of an eyeball (for example, a distance between the center of corneal curvature C of the cornea 501 and the center of the pupil S or a radius of curvature of the cornea 501), arrangement of a retina or optic nerves in an eyeball, or the like, and thus there are individual differences. Thus, there is an error unique to a user between the visual line of the user estimated based on the visual line vector 550 of the user and a direction in which the user actually views the display surface. In the embodiment, in consideration of such circumstances, a calibration process is performed for each user to acquire eyeball information regarding the eyeball 500 of the user including at least a correlation between the visual line vector 550 and a direction in which the user actually views the display surface 530. Then, a visual line of the user is detected by performing a process of correcting the visual line vector 550 based on the acquired eyeball information which is information unique to the user. Accordingly, in the embodiment, it is possible to perform the visual line detection process with higher precision.

[3-2. Light Source Driving Control]

Next, the driving control of the light source based on the predetermined driving condition at the time of the acquisition of the captured image of the eyeball of the user in the visual line vector calculation process will be described. As described in the foregoing <1. Outer appearance and overall configuration of visual line detection device> and <2. Configuration of visual line detection device>, the plurality of LEDs 141 to 148 are arranged as the light sources in the embodiment, as illustrated in FIG. 2B. The driving of the LEDs 141 to 148 is selectively controlled based on the predetermined driving condition by the light source driving control unit 212 illustrated in FIG. 3.

The driving control of the LEDs 141 to 148 by the light source driving control unit 212 will be described with reference to FIGS. 5A to 5F. FIGS. 5A to 5F are explanatory diagrams for describing the driving control of the light sources in the visual line detection process according to the embodiment. In FIGS. 5A to 5F, the light source substrate 140 and the LEDs 141 to 148 illustrated in FIGS. 1, 2A, and 2B are schematically illustrated and light emission patterns of the LEDs 141 to 148 which can be performed in the driving control of the LEDs 141 to 148 are illustrated. In FIGS. 5A to 5F, among the LEDs 141 to 148, the LED emitting light, that is, the LED radiating light to the eyeball of the user, are expressed by hatching.

Figure 5A:
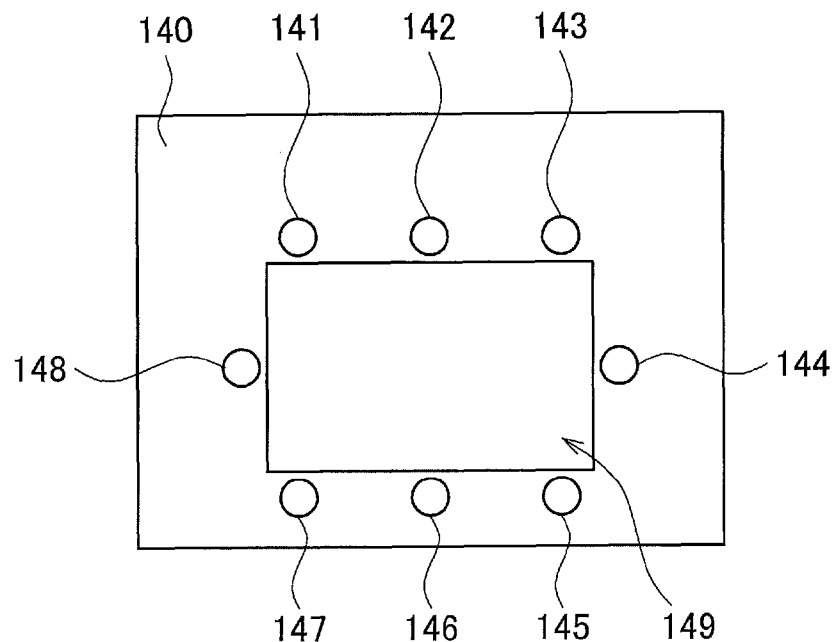
FIG. 5A is an explanatory diagram for describing light source driving control in a visual line detection process according to the embodiment.

Referring to FIG. 5A, a light emission pattern in which none of the LEDs 141 to 148 are driven is illustrated. For example, when the visual line detection process is not performed, the light source driving control unit 212 drives the LEDs 141 to 148 under a driving condition shown in FIG. 5A. When the visual line detection process is not performed, power consumption is reduced due to the fact that the LEDs 141 to 148 are not driven.

Figure 5B:
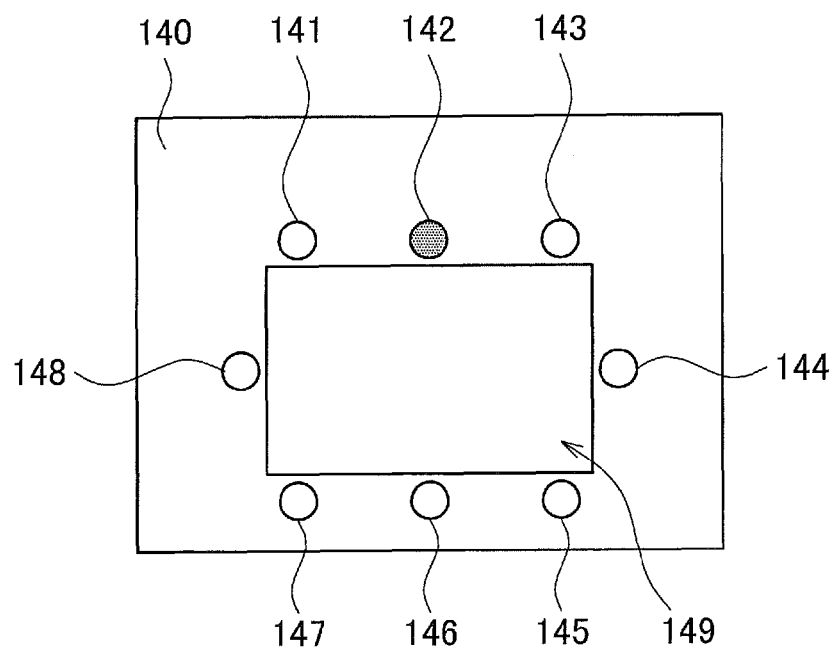
FIG. 5B is an explanatory diagram for describing light source driving control in a visual line detection process according to the embodiment.

Referring to FIG. 5B, a light emission pattern in which only one LED of the LEDs 141 to 148 is driven is illustrated. In the example illustrated in FIG. 5B, only the LED 142 is driven among the LEDs 141 to 148. In this way, the light source driving control unit 212 can selectively drive any LED among the plurality of LEDs 141 to 148.

Figure 5C:
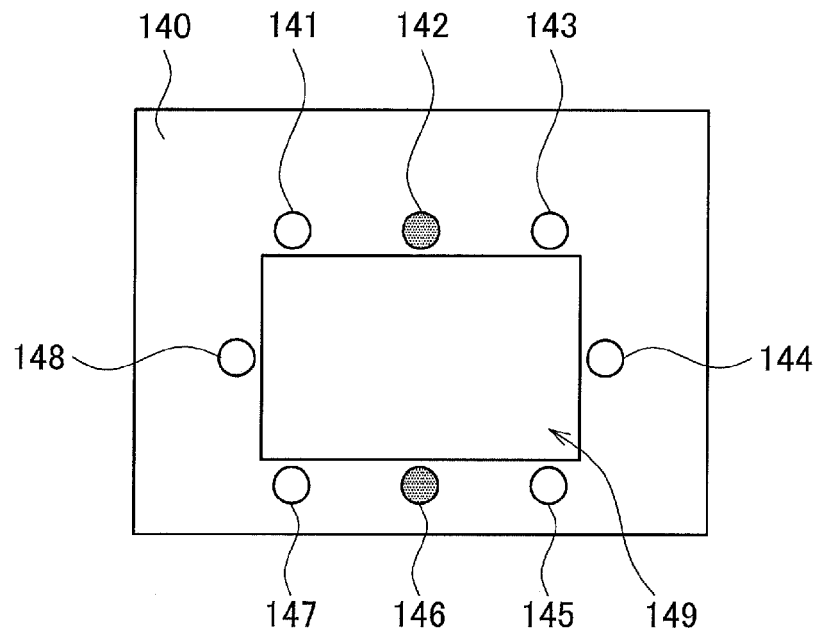
FIG. 5C is an explanatory diagram for describing light source driving control in a visual line detection process according to the embodiment.
Figure 5D:
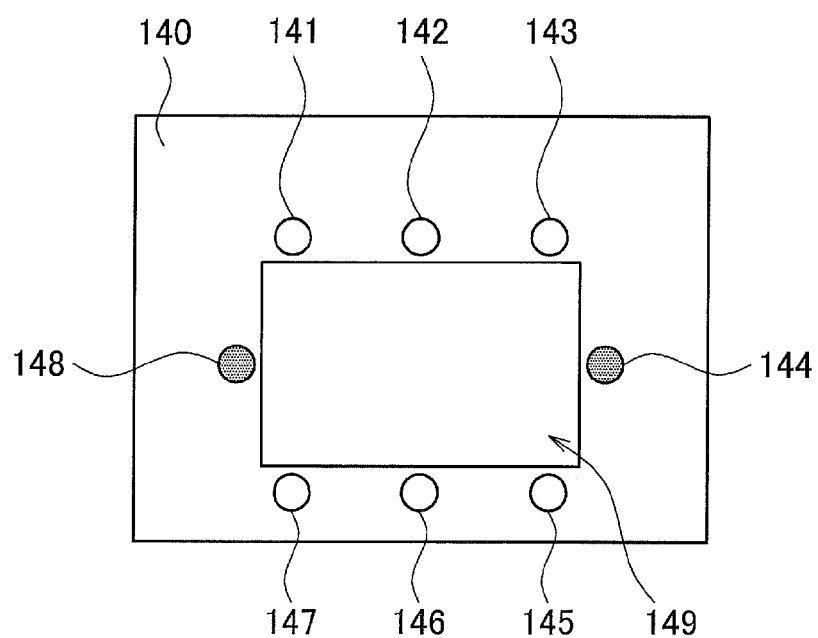
FIG. 5D is an explanatory diagram for describing light source driving control in a visual line detection process according to the embodiment.

Referring to FIGS. 5C and 5D, light emission patterns in which only two LEDs of the LEDs 141 to 148 are driven are illustrated. In the example illustrated in FIG. 5C, only the LEDs 142 and 146 located in the vertical direction are driven among the LEDs 141 to 148. In the example illustrated in FIG. 5D, only the LEDs 144 and 148 located in the horizontal direction are driven among the LEDs 141 to 148. Thus, the light source driving control unit 212 can cause light to be radiated in two direction symmetric with respect to the eyeball of the user by driving only two LEDs located in the vertical direction with respect to the eyeball of the user or only two LEDs located in the horizontal direction with respect to the eyeball of the user.

Figure 5E:
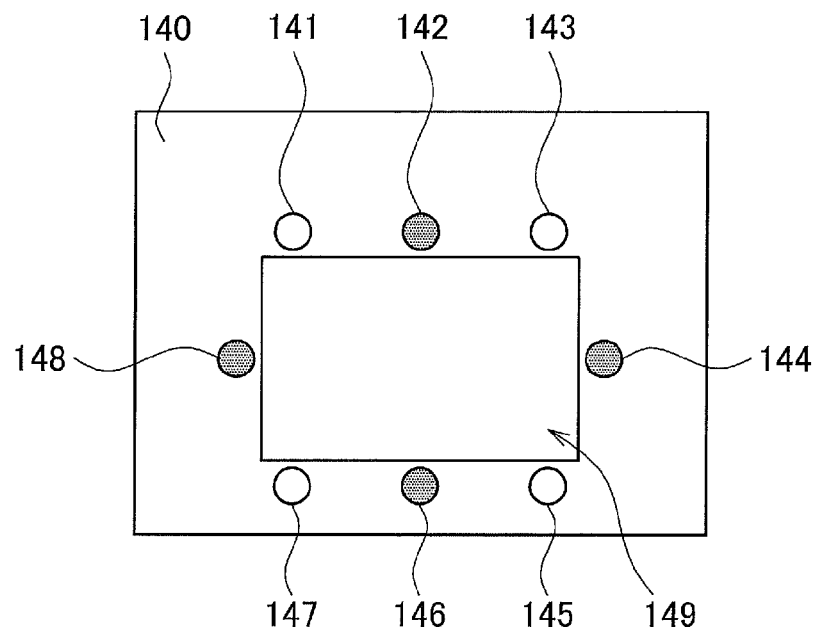
FIG. 5E is an explanatory diagram for describing light source driving control in a visual line detection process according to the embodiment.
Figure 5F:
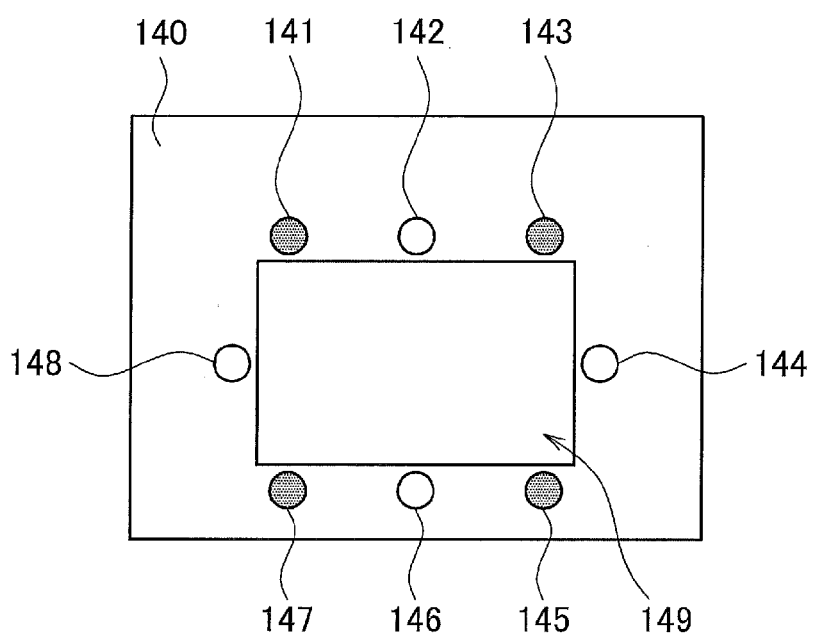
FIG. 5F is an explanatory diagram for describing light source driving control in a visual line detection process according to the embodiment.

Referring to FIGS. 5E and 5F, light emission patterns in which only four LEDs are driven among the LEDs 141 to 148 are illustrated. In the example illustrated in FIG. 5E, only the LEDs 142, 144, 146, and 148 located in the vertical and horizontal directions are driven among the LEDs 141 to 148. In the example illustrated in FIG. 5F, only the LEDs 141, 143, 145, and 147 located near the vertexes of the substantially rectangular opening 149 are driven among the LEDs 141 to 148. Thus, the light source driving control unit 212 can cause light to be radiated in four directions symmetric with respect to the eyeball of the user by driving only four LEDs located in the vertical and horizontal directions with respect to the eyeball of the user or only four LEDs located in oblique directions with respect to the eyeball of the user.

Here, as described with reference to FIG. 4 in the foregoing [3-1. Visual line vector calculation process], the 3-dimensional coordinates of the center of corneal curvature C of the cornea 501 are calculated based on the Purkinje image 504 by the light radiated from the light source 520 in the visual line vector calculation process. In the example illustrated in FIG. 4, this calculation process is performed based on one Purkinje image 504 formed by the light radiated from one light source 520. However, when there are a plurality of Purkinje images, a process of calculating 3-dimensional coordinates of the center of corneal curvature C of the cornea 501 may be performed for each of the Purkinje images. Then, the final 3-dimensional coordinates of the center of corneal curvature C of the cornea 501 may be calculated by obtaining an average value, a median value, or the like of the calculation results based on the Purkinje images. Accordingly, by using a plurality of different Purkinje images, it is possible to further improve the precision of the calculated 3-dimensional coordinates of the center of corneal curvature C of the cornea 501. In the embodiment, for example, as illustrated in FIGS. 5C to 5F, a plurality of different Purkinje images can be formed by driving the plurality of LEDs 141 to 148. Therefore, it is possible to further improve the precision of the calculated 3-dimensional coordinates of the center of corneal curvature C of the cornea 501.

In the embodiment, as illustrated in FIGS. 2B and 5A to 5F, the LEDs 141 to 148 are installed along the edge of the opening 149. Accordingly, the light is radiated relatively to the front side with respect to the cornea of the eyeball of the user, that is, in a direction closer to a visual axis (direction of the visual line vector) of the eyeball of the user. By radiating the light in the direction closer to the visual axis of the eyeball of the user and acquiring a captured image of the eyeball according to the reflected light of the radiated light from the eyeball, the eyeball can be photographed on substantially the front side. Therefore, since distortion or the like near the center of the captured image of the eyeball is reduced, the precision of the detection of the image of the pupil is further improved.

In the embodiment, the driving conditions of the LEDs 141 to 148 which are light sources may be set according to observation state information regarding a state in which the user observes the display surface. Here, the observation state information is information unique to the user and includes at least one of information regarding the shape of an eye of the user, information regarding whether the user wears glasses, and information regarding a direction in which the user observes the display surface of the visual line detection device 10.

The information regarding the shape of an eye of the user includes, for example, information regarding the sizes or shapes of an eyeball, a cornea, and an eyelid and a positional relation, a ratio, or the like between the eyeball and the cornea. The process of calculating the center of corneal curvature C of the cornea 501 has been described in the foregoing [3-1. Visual line vector calculation process]. However, in consideration of the calculation principle, the Purkinje image 504 in the captured image 540 is preferably located on the cornea 501. There is an individual difference in the shape of an eye. For example, when light is radiated from one light source, the Purkinje image 504 may not be located on the cornea 501 in some cases according to a positional relation between the light source and the eyeball. For example, when a user has the shape of a relatively thin eye, light radiated from one light source installed at a predetermined position may be considered to be blocked by an eyelid depending on the shape of the eyelid and the light may not be radiated appropriately to the eyeball of the user. Accordingly, in the embodiment, as illustrated in FIGS. 5A to 5F, the plurality of LEDs 141 to 148 arranged at different positions with respect to the eyeball are selectively driven. Hence, the LEDs 141 to 148 to be driven may be appropriately selected according to the information regarding the shape of the eye of the user so that the Purkinje image 504 is located at an appropriate position. Thus, in the embodiment, since the driving control of the light sources can be performed according to the information regarding the shape of the eye of the user, the Purkinje image 504 is reliably detected on the cornea 501.

For example, when a user wears glasses and light is radiated from the light source to his or her eyeball, there is a probability of an image of his or her pupil or a Purkinje image being difficult to detect from a captured image of his or her eyeball due to reflected light from lenses of the glasses. On the other hand, in the embodiment, for example, as illustrated in FIGS. 5A to 5F, diverse light emission patterns are realized by selectively driving the plurality of LEDs 141 to 148 arranged at different positions with respect to the eyeball. Hence, in the visual line vector calculation process, a light emission pattern in which the reflection of the light from the lenses of the glasses has relatively little influence on the detection of an image of a pupil or a Purkinje image may be appropriately selected among the diverse light emission patterns. Since a preferred light emission pattern is different depending on the shapes of the frame of glasses, lenses, or the like, the driving conditions of the LEDs 141 to 148 realizing an optimum light emission pattern may be set for each user. For example, an optimum light emission pattern is searched for by specifying the positions of the LEDs 141 to 148 which are causes hindering the detection of an image of a pupil or a Purkinje image by actually allowing the LEDs 141 to 148 to sequentially emit light to a user wearing glasses. When the number of LEDs 141 to 148 driven in an optimum light emission pattern is small and an amount of light is insufficient, a process of increasing an output for driving the LEDs or increasing exposure or a gain of the imaging unit 160 may be appropriately performed. When considerably suitable light emission patterns can be generally set to some extent depending on whether a user wears glasses, a driving condition for realizing a considerably suitable light emission pattern at the time of the wearing of the glasses and a driving condition for realizing a considerably suitable light emission pattern at the time of viewing with the naked eye may be set in advance and a suitable light emission pattern may be selected from these driving conditions according to the information regarding whether the user wears the glasses. Thus, in the embodiment, since the driving control of the light source can be performed according to the information regarding whether the user wears glasses, it is possible to detect the image of the pupil or the Purkinje image from the captured image of the eyeball with higher precision.

For example, when the visual line detection device 10 according to the embodiment is an EVF connected to the imaging device 20, there is a probability of a positional relation between the user and the light source being changed since a direction in which the user observes the display surface of the visual line detection device 10 is changed depending on whether the user grasps the imaging device 20 in the lateral direction or the longitudinal direction. For example, when the user grasps the imaging device 20 in the lateral direction, the y-axis direction of the visual line detection device 10 illustrated in FIG. 1 can become the vertical direction for the user. However, when the user grasps the imaging device 20 in the longitudinal direction, a relation between the vertical direction and the horizontal direction for the user can be reversed and the x-axis direction of the visual line detection device 10 illustrated in FIG. 1 can become the vertical direction for the user. Thus, when the direction in which the user observes the display surface of the visual line detection device 10 is changed, a positional relation between the eye of the user and the LEDs 141 to 148 is changed, and thus there is a probability of the suitable driving condition of the LEDs 141 to 148 also being changed. In the embodiment, the LEDs 141 to 148 to be driven may be appropriately selected so that the visual line vector calculation process can be appropriately performed based on information regarding the direction in which the user observes the display surface of the visual line detection device 10. For example, by installing a sensor device detecting a posture in the visual line detection device 10 or the imaging device 20, the information regarding the direction in which the user observes the display surface of the visual line detection device 10 can be acquired based on a posture of the visual line detection device 10 detected by the sensor device.

In the embodiment, as described above, the optimum driving condition of the light source may be appropriately set for each user based on the observation state information which is information unique to the user. Thus, by setting the optimum driving condition of the light source for each user based on the observation state information, the precision of the visual line vector calculation process is further improved and the precision of the visual line detection is further improved. The optimum driving condition of the light source for each user based on the observation state information may be acquired during the visual line detection process or before the visual line detection process according to the embodiment by actually performing the visual line detection process on the user while sequentially changing the combinations of the LEDs 141 to 148 to be driven or the intensity of the radiated light and comparing the detection results. When the driving conditions of the LEDs 141 to 148 are acquired during the visual line detection process, the driving conditions of the LEDs may be dynamically changed based on the acquired driving conditions during the visual line detection process (the visual line vector calculation process).

[3-3. Calibration Process]

Next, the calibration process performed by the calibration processing unit 214 will be described in detail. As described in the foregoing <2. Configuration of visual line detection device>, the eyeball information regarding the eyeball of the user including at least the correlation between the visual line vector of the user and the direction in which the user views the display surface of the display unit 110 is acquired in the calibration process. Specifically, in the calibration process according to the embodiment, a calibration image in which a marker is superimposed and displayed on content is displayed on the display surface of the display unit 110 of the visual line detection device 10. Then, a correlation between the visual line vector of the user and the coordinates of a position at which the marker is displayed on the display surface is acquired when the visual line detection processing unit 213 calculates the visual line vector of the user while the visual line is directed toward the marker The details of the calibration process will be described with reference to FIGS. 6A to 6C. FIGS. 6A to 6C are explanatory diagrams for describing the calibration process according to the embodiment.

Referring to FIGS. 6A to 6C, a display surface 610 observed by the user at the time of execution of the calibration process is illustrated. The display surface 610 corresponds to the display surface 111 of the display unit 110 of the visual line detection device 10 illustrated in FIGS. 1, 2A, and 3. The display of the display surface 610 at the time of execution of the calibration process may be controlled by the display control unit 211 illustrated in FIG. 3 according to an instruction from the calibration processing unit 214.

FIG. 6A illustrates the display surface 610 at a step prior to the calibration process. At the step prior to the calibration process, a through image 611 is displayed on the display surface 610.

FIG. 6B illustrates the display surface 610 during the execution of the calibration process. During the execution of the calibration process, a calibration image is displayed on the display surface 610. In the calibration image, the through image 611 is displayed on the display surface 610 in a darkened state (a state in which luminance is lowered). In the calibration image, markers 612a to 612e are sequentially displayed on the darkened through image 611. The markers 612a to 612e are displayed, for example, as light spots with a predetermined area. When the through image 611 is displayed in the darkened state in the calibration image, the user can direct his or her visual line toward the markers 612a to 612e without being distracted by the through image 611, and thus the calibration process can be efficiently performed. In the calibration image, the through image 611 may not be displayed temporarily and only the markers 612a to 612e may be displayed sequentially on the display surface 610.

Specifically, when the calibration process starts, the calibration image in which the marker 612a is superimposed on the darkened through image 611 is first displayed on the display surface 610 according to an instruction from the calibration processing unit 214. The calibration processing unit 214 can instruct the display control unit 211 to display coordinates of the marker 612a on the display surface 610. For example, as illustrated in FIG. 6B, the marker 612a is displayed at substantially the center of the display surface 610.

When the marker 612a is displayed, the user performs an action of directing his or her visual line toward the marker 612a. The visual line vector of the user when the visual line is directed toward the marker 612a is calculated by the visual line detection processing unit 213 and the calculation result is transmitted to the calibration processing unit 214. Since the calibration processing unit 214 has information regarding the coordinates of the marker 612a at the display position on the display surface 610, the calibration processing unit 214 can acquire a correlation between the visual line vector of the user and the coordinates of the marker 612a actually viewed by the user at the display position on the display surface 610.

When the foregoing correlation is acquired in regard to the marker 612a, the display of the display surface 610 is changed according to an instruction from the calibration processing unit 214. Specifically, the display of the marker 612a disappears from the display surface 610 and the marker 612b is newly displayed. In the example illustrated in FIG. 6B, the marker 612b is displayed near substantially the center of the upper side of the display surface 610. Then, as in the case of the marker 612a, the calibration processing unit 214 acquires a correlation between the visual line vector of the user and the coordinates of the marker 612b at a display position on the display surface 610 in regard to the marker 612b.

Subsequently, likewise, the markers 612c, 612d, and 612e are sequentially displayed and the calibration processing unit 214 acquires a correlation between the visual line vector based on the direction of the eyeball of the user and the coordinates of each marker at a display position on the display surface 610 for each marker. In the example illustrated in FIG. 6B, the markers 612c, 612d, and 612e are displayed near substantially the centers of the right side, the lower side, and the left side of the display surface 610. When the calibration processing unit 214 acquires the correlation in regard to each of the markers 612a to 612e, the calibration process ends. As illustrated in FIG. 6B, by displaying the markers 612a to 612e at the substantial center and near the sides of the display surface 610, the correlations are acquired on nearly the entire region of the display surface 610, and thus the precision of the visual line detection is further improved.

As illustrated in FIG. 6C, when the calibration process ends, the display of the display surface 610 returns to the through image 611 with the normal luminance. After the calibration process ends, the visual line of the user on the display surface 610 is detected by appropriately correcting the visual line vector of the user based on the correlation acquired in the calibration process. Specifically, the visual line detection processing unit 213 can perform a process of correcting coordinates estimated from the visual line vector of the user on the display surface 610 to coordinates actually viewed by the user on the display surface 610. As illustrated in FIG. 6C, for example, a marker 613 indicating a visual line of the user may be displayed in a region corresponding to the visual line of the user on the display surface 610 subjected to the correction process.

The details of the calibration process according to the embodiment have been described above with reference to FIGS. 6A to 6C. As described above, in the calibration process according to the embodiment, for example, the plurality of markers 612a to 612e are sequentially displayed at different positions of the display surface 610 and the correlation between the visual line vector of the user and the coordinates of the display position of each of the markers 612a to 612e on the display surface 610 is acquired in regard to each of the markers 612a to 612e. Since the correlation has a different value in accordance with the shape or size of the eyeball, the correlation is information unique to the user. In the embodiment, the visual line of the user on the display surface 610 is detected by performing the process of correcting the visual line vector based on the eyeball information regarding the eyeball of the user including at least the correlation. Accordingly, since the visual line detection process is performed in consideration of an individual difference of the user, the precision of the visual line detection is further improved. The eyeball information may include various parameters (for example, the distance between the center of corneal curvature C of the cornea and the center of pupil S and the radius of the curvature of the cornea) indicating the structure of the eyeball of the user. The parameters are parameters that have a numerical value unique to the user and are used in the visual line vector calculation process. In the visual line vector correction process, a process of correcting the calculated visual line vector based on the parameters may be further performed.

In the calibration image illustrated in FIG. 6B, display of the markers 612a to 612e may be controlled such that the colors of the markers 612a to 612e are changed while the user directs his or her visual line toward the markers 612a to 612e. When the colors of the markers 612a to 612e are changed, the user can recognize that his or her visual line is currently being detected. For example, determination regarding whether the user directs his or her visual line toward the markers 612a to 612e, which is a criterion of the change in the colors of the markers 612a to 612e, may be performed based on stop of a motion of the eyeball of the user in the captured image of the eyeball by the visual line detection processing unit 213.

In the example illustrated in FIG. 6B, the five markers 612a to 612e are used in the calibration process, but the embodiment is not limited to this example. In the embodiment, predetermined precision may be obtained in the visual line detection process and the number of markers or the display positions of the markers displayed in the calibration process may be appropriately set.

[3-4. Process of Reading Unique User Information Based on Iris Authentication]

In the embodiment, as described above, the driving condition of the light source 190 based on the observation state information and the information unique to the user, such as the eyeball information, may be stored in a storage unit or the like in association with the user. The information unique to the user may be read and used in the visual line detection process, as necessary. Personal authentication or individual identification using iris authentication can be applied to the process of reading the information unique to the user. For example, when the visual line detection device 10 is used, a personal authentication process or an individual identification process of the user is performed using iris authentication and corresponding information that is unique to the user is read based on a result of the process. As described in the foregoing [3-1. Visual line vector calculation process], in the visual line detection process according to the embodiment, the captured image of the eyeball 500 of the user is acquired by the imaging unit 160 in the visual line vector calculation process. Therefore, an image of an iris included in the captured image can be used in the personal authentication or the individual identification. Thus, in the embodiment, both of the visual line vector calculation process and the iris authentication process may be performed based on the captured image of the eyeball 500 of the user acquired by the imaging unit 160. By performing the iris authentication process based on the captured image of the eyeball 500 of the user used in the visual line vector calculation process, it is possible to perform the personal authentication or the individual identification of the user without providing a separate configuration.

Here, the overview of the iris authentication process will be described in brief. In the iris authentication process according to the embodiment, for example, a Daugman algorithm can be used.

In the iris authentication process according to the embodiment, an image of a part corresponding to an iris is first extracted from the captured image of the eyeball of the user. The captured image of the eyeball of the user may be a captured image photographed in the visual line vector calculation process. In the detection of a part corresponding to an iris, various image processing methods used in the process of detecting the image of the pupil 503 or the Purkinje image 504 described in the foregoing [3-1. Visual line vector calculation process] may be used.

Next, the extracted image (iris image) of the iris part is converted into digital information (for example, a bit string) including information indicating characteristics unique to the user by a lossy compression process based on a predetermined mathematical method. The digital information generated by performing a mathematical process on the iris image in this way is extracted as the characteristics unique to the individual and is also referred to as a digital template. The bit string which is the digital template includes basic information as far as statistically meaningful comparison can be performed in comparison with other iris images. For example, in the Daugman algorithm, a plurality of complex number groups including a local amplitude and phase information of the iris image are acquired by extracting a space frequency range with a predetermined SN ratio in consideration of performance such as a resolution of the imaging unit 160 from the iris image using wavelet transform by a Gabor filter. Then, based on the plurality of complex number groups, a bit string of 2048 bits including only sign bits of the complex numbers expressing a Gabor region without inclusion of the amplitude information is acquired as a bit string corresponding to the iris image. Since an influence of a difference of illumination or a color of an iris at the time of the photographing of the eyeball can be excluded by allowing the bit string to include no amplitude information, a more stable digital template is acquired for a long time.

Next, values of the bit string acquired based on the iris image are compared to values of a bit string registered in advance as a digital template. When the Hamming distance of the values of both bit strings is less than a predetermined threshold value, both of the bit strings are determined to be identical. The values of the bit strings acquired based on the iris image may be compared to the values of a plurality of bit strings registered in advance (individual identification: one-to-multiple matching) or may be compared to the values of a specific bit string registered in advance and corresponding to a specific user (personal authentication: one-to-one matching). Since the Daugman algorithm is a method widely used in a general iris authentication process, further detailed description of the Daugman algorithm will be omitted in this section.

In the embodiment, a user attempting to use the visual line detection device 10 may be specified based on the above-described iris authentication process and unique information corresponding to the user may be read. Then, the visual line vector correction process is performed using the read information that is unique to the user.

Here, the bit string may be, for example, a bit sequence arranged in a 2-dimensional form. By detecting a shift amount between the bit sequence acquired from the iris image of the user and a bit sequence registered in advance as a digital template, an angle (direction) of the eyeball of the user can be calculated. In the embodiment, information regarding an angle of the eyeball of the user gained during the iris authentication process may be further used in the visual line vector correction process.

4. Modification Examples

Next, modification examples of the visual line detection process according to the embodiment will be described. In the following [4-1. Addition of IR filter], other configuration examples when the visual line detection process according to the embodiment is likewise applied to an EVF of an imaging device will be described. In the following [4-2. Application to wearable device] and [4-3. Application to head-mounted display], cases in which the visual line detection process according to the embodiment is applied to other devices will be described.

[4-1. Addition of IR Filter]

In one modification example of the visual line detection device according to the embodiment, infrared light from a light source is radiated to an eyeball of a user. An infrared light passing mechanism shielding light with a wavelength band other than an infrared band is installed in the front stage of an imaging unit. Thus, reflected light of the infrared light from the eyeball of the user passes through the infrared light passing mechanism and is subsequently incident on the imaging unit. Thus, when the infrared light passing mechanism is installed in the front stage of the imaging unit, light other than the infrared light which may be noise is prevented from being incident on the imaging unit. Therefore, it is possible to acquire a captured image of the eyeball of the user more vividly.

A specific configuration of such one modification example of the visual line detection device according to the embodiment will be described with reference to FIG. 7. FIG. 7 is a sectional view illustrating another configuration example when the visual line detection process according to the embodiment is applied to an EVF of an imaging device.

Referring to FIG. 7, a visual line detection device 70 according to a modification example of the embodiment includes a display unit 110, an optical path changing element 120, a magnifier unit 130, a light source substrate 140, an eyecup 150, an imaging unit 160, a hinge 170, and an infrared filter (IR filter) 710. Here, since the functions and the configurations of the display unit 110, the optical path changing element 120, the magnifier unit 130, the light source substrate 140, the eyecup 150, the imaging unit 160, and the hinge 170 among the constituent elements of the visual line detection device 70 according to the modification example are the same as the functions and the configurations of the display unit 110, the optical path changing element 120, the magnifier unit 130, the light source substrate 140, the eyecup 150, the imaging unit 160, and the hinge 170 of the visual line detection device 10 illustrated in FIGS. 1, 2A, and 2B, detailed description of these constituent elements will be omitted. The visual line detection device 70 according to the modification example corresponds to a device in which the IR filter 710 is added to the visual line detection device 10 illustrated in FIGS. 1, 2A, and 2B. The sectional view illustrated in FIG. 7 corresponds to the sectional view illustrated in FIG. 2A and is a sectional view on a plane (y-z plane) defined by the y axis and the z axis of the visual line detection device 70 according to the modification example.

As illustrated in FIG. 7, the IR filter 710 is arranged between the optical path changing element 120 and the imaging unit 160 in the visual line detection device 70 according to the modification example. The IR filter 710 is an example of an infrared light passing mechanism having a function of passing infrared light and shielding light with a wavelength band other than the infrared light.

On the other hand, in the modification example, a light source (not illustrated in FIG. 7) arranged in the light source substrate 140 is configured by an LED emitting infrared light. Accordingly, in the modification example, a captured image of an eyeball of a user is acquired when the infrared light is radiated to the eyeball of the user and the imaging unit 160 detects reflected light of the infrared light from the eyeball. By using light, such as infrared light, other than light with a visible light band as light radiated to the eyeball of the user, the user is not startled by the light radiated from the light source, and thus the radiated light does not hinder the user from observing the display surface 111. Since light which has a wavelength band other than the infrared light and may thus become noise is shielded by the IR filter 710 installed between the optical path changing element 120 and the imaging unit 160, the imaging unit 160 detects the reflected light from the eyeball with higher precision, and thus the more vivid captured image of the eyeball can be acquired.

The configuration in which the IR filter 710 is used as the infrared light passing mechanism has been described above. In the modification example, however, various other optical members may be applied as long as the optical members are optical members having a function of shielding light with a wavelength band other than the infrared light. For example, in the modification example, the IR filter 710 may not be installed, but the optical path changing element 120 may instead have a function of an infrared light passing mechanism reflecting the infrared light in a predetermined direction and linearly passing light with other wavelengths. For example, the optical path changing element 120 may be a dichroic mirror or have a function of reflecting infrared light incident in the z-axis direction in the positive direction of the y axis and passing light which is incident in the z-axis direction and has other wavelength bands while maintaining a traveling direction of the light. When the optical path changing element 120 has such a function, light which has the wavelength band other than the infrared light and may thus become noise is shielded and the infrared light is thus efficiently incident on the imaging unit 160. Accordingly, as in the case in which the IR filter 710 is installed, the imaging unit 160 can detect the reflected light from the eyeball with higher precision, and thus the more vivid captured image of the eyeball is acquired.

As described above with reference to FIG. 7, according to the modification example, infrared light is radiated from the light source to the eyeball of the user, the infrared light passing mechanism shielding light with a wavelength other than the infrared band is installed in the front stage of the imaging unit, and the reflected light of the infrared light from the eyeball of the user passes through the infrared light passing mechanism and is subsequently incident on the imaging unit. Accordingly, it is possible to further obtain the advantage of acquiring a more vivid captured image of the eyeball in addition to the advantages obtained by the visual line detection device 10 according to the embodiment.

[4-2. Application to Wearable Device]

Next, a modification example in which the visual line detection process according to the embodiment is applied to a device other than the imaging device will be described. The visual line detection process according to the embodiment can be applied to, for example, a glasses-type wearable device.

Figure 8:
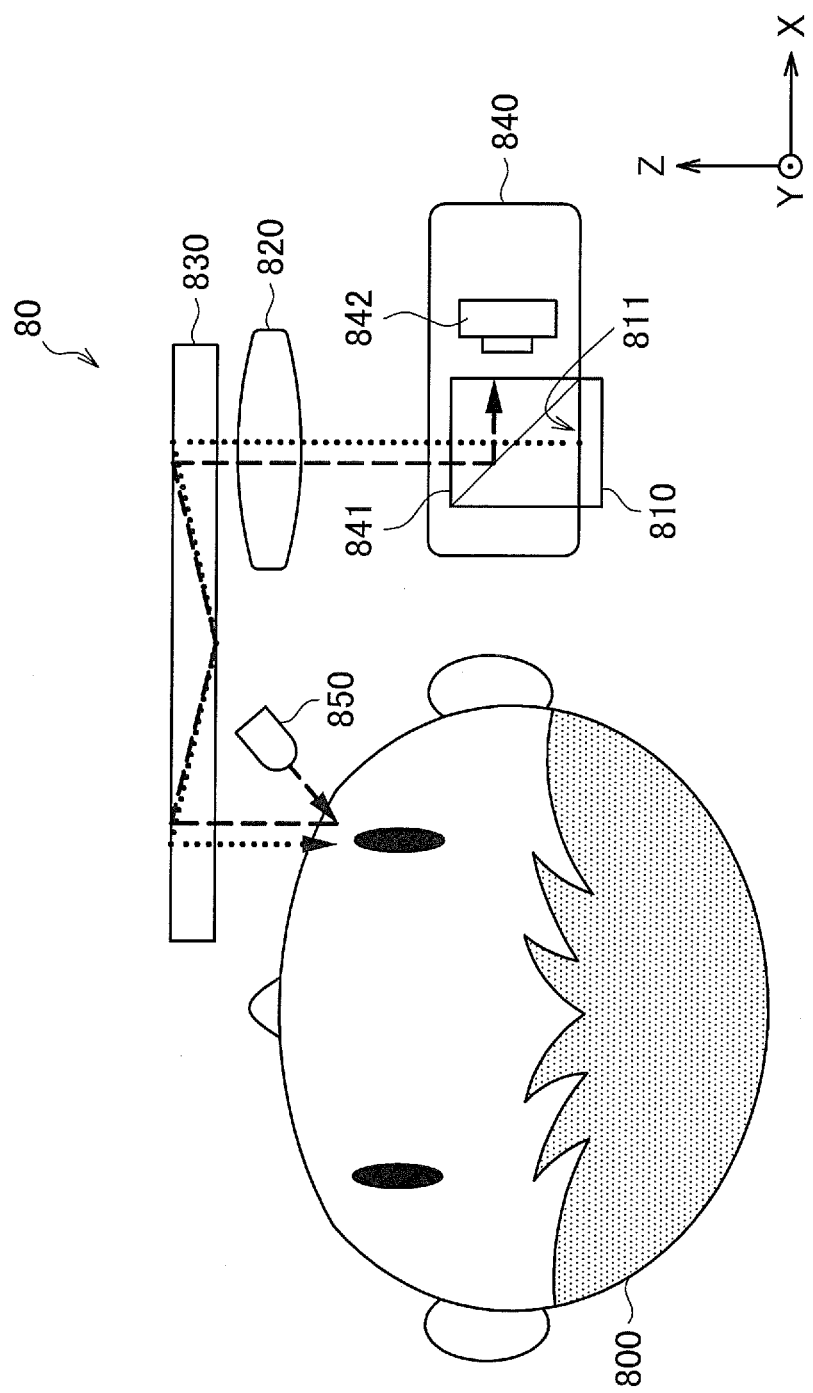
FIG. 8 is a schematic diagram illustrating an example of the configuration of a glasses-type wearable device to which the visual line detection process according to the embodiment is applied.

An overall configuration of a glasses-type wearable device to which the visual line detection process according to the embodiment is applied will be described with reference to FIG. 8. FIG. 8 is a schematic diagram illustrating an example of the configuration of the glasses-type wearable device to which the visual line detection process according to the embodiment is applied. In the description of the modification example, the visual line detection device according to the embodiment refers to a glasses-type wearable device to which the visual line detection process according to the embodiment is applied unless otherwise mentioned.

Referring to FIG. 8, a visual line detection device 80 is a glasses-type wearable device and includes a display unit 810, a lens 820, a light guide member 830, a visual line detection unit 840, and a light source 850. In FIG. 8, a user 800 wearing the visual line detection device 80 is illustrated along with the visual line detection device 80. An optical path of light between the visual line detection device 80 and the eyeball of the user 800 within the visual line detection device 80 is indicated by an arrow. FIG. 8 schematically illustrates a case in which the user 800 wearing the visual line detection device 80 is viewed from above. In the following description of the modification example, as illustrated in FIG. 8, a direction in which the user 800 faces is defined as a Z-axis direction. When viewed by the user 800, the horizontal direction is defined as an X-axis direction and the vertical direction is defined as a Y-axis direction. A direction of the Z axis in which the user views is defined as a positive direction of the Z axis, and the right side of the X axis when viewed by the user is defined as a positive direction of the X axis.

The display unit 810 corresponds to the display unit 110 of the visual line detection device 10 illustrated in FIGS. 1 and 2A. For example, the display unit 810 is arranged beside the user 800 and a display surface 811 is arranged in the positive direction of the Z axis. Any content can be displayed on the display surface 811 of the display unit 810. Light (that is, light forming the content) from the display surface 811 sequentially passes through the visual line detection unit 840, the lens 820, and the light guide member 830 in the positive direction of the Z axis and is incident on an eyeball of the user 800. In FIG. 8, an optical path of the light from the display surface 811 is indicated by a dotted-line arrow.

The visual line detection unit 840 includes an optical path changing element 841 and an imaging unit 842. The light from the display surface 811 of the display unit 810 is transmitted through the optical path changing element 841 linearly in the positive direction of the Z axis and is incident on the lens 820. The optical path changing element 841 and the imaging unit 842 correspond to the optical path changing element 120 and the imaging unit 160 of the visual line detection device 10 illustrated in FIGS. 1 and 2A. The optical path changing element 841 has the same function and configuration as the optical path changing element 120 and is an optical member that has a mirror function of linearly transmitting light incident in one direction and reflecting light (or a part of the light) coming from another direction in a predetermined direction. Specifically, the optical path changing element 841 is, for example, a beam splitter, and transmits light incident in the negative direction of the Z axis while maintaining a traveling direction of the light and reflects light incident in the positive direction of the Z axis in the positive direction of the X axis. The imaging unit 842 is installed in the positive direction of the X axis to be adjacent to the optical path changing element 841 so that a light reception surface faces the optical path changing element 841.

The lens 820 is an optical member that has a function of expanding display of content on the display surface 811 of the display unit 810 at predetermined magnification. The lens 820 corresponds to the magnifier unit 130 of the visual line detection device 10 illustrated in FIGS. 1 and 2A. In the example illustrated in FIG. 8, a single lens is illustrated as the lens 820. However, in the visual line detection device 80, a lens system in which a plurality of various lenses are combined and appropriately adjusted to expand and display the content at predetermined magnification may be installed instead of the lens 820. The light from the display surface 811 passes through the lens 820 in the positive direction of the Z axis and is incident on the light guide member 830.

The light guide member 830 is a plate-shaped or sheet-shaped optical member and can guide light in a direction parallel to a plane inside the plate or the sheet. In the modification example, for example, a hologram sheet is used as the light guide member 830. The light guide member 830 is arranged to be substantially parallel to the X-Y plane (a plane defined by the X and Y axes) and a partial region of the light guide member 830 faces an eyeball of the user 800. The light from the display surface 811 is transmitted through the lens 820, travels in the positive direction of the Z axis, and is incident on the light guide member 830. The light incident on the light guide member 830 is guided in a direction parallel to the X-Y plane inside the light guide member 830 and arrives at the eyeball of the user 800, for example, as indicated by the dotted-line arrow in FIG. 8. Thus, the user can observe the display surface 811 of the display unit 810 through the optical path changing element 841, the lens 820, and the light guide member 830.

The light source 850 radiates light to an eyeball of the user observing the display surface 811 of the display unit 810. For example, the light source 850 may be an LED and may radiate infrared light. The light source 850 corresponds to the LEDs 141 to 148 which are the light sources of the visual line detection device 10 illustrated in FIG. 2B. In the example illustrated in FIG. 8, the single light source 850 is illustrated. However, the visual line detection device 80 may include a plurality of light sources that radiate light to an eyeball of the user 800 from different directions, as in the visual line detection device 10. The light source 850 may be fixed to another constituent element (including a frame or a temple (not illustrated) mounting the visual line detection device 80 on the user 800) of the visual line detection device 80 by a supporting member (not illustrated).

Reflected light from the eyeball of the user 800, which is reflected light of the light radiated from the light source 850, follows an optical path which the light from the display surface 811 of the display unit 810 follows in a reverse direction and arrives at the optical path changing element 841. That is, the reflected light from the eyeball of the user 800 sequentially passes through the light guide member 830 and the lens 820 and arrives at the optical path changing element 841. As described above, since the optical path changing element 841 has the function of reflecting the light incident in the positive direction of the Z axis in the positive direction of the X axis, the optical path of the reflected light is changed by the optical path changing element 841 and the reflected light is incident on the imaging unit 842. Thus, the imaging unit 842 detects the reflected light from the eyeball of the user 800 and acquires a captured image of the eyeball of the user 800. In FIG. 8, an optical path along which the light radiated from the light source 850 is reflected from the eyeball of the user 800 and arrives at the imaging unit 842 is indicated by a dashed line arrow.

As in the visual line detection device 10, the visual line detection device 80 also performs a visual line detection process for the user 800 on the display surface 811 of the display unit 810 based on the captured image of the eyeball of the user 800 acquired by the imaging unit 842. As the visual line detection process of the visual line detection device 80, the same process as the visual line detection process of the visual line detection device 10 described in the foregoing <3. Details of visual line detection process> may be performed.

The overall configuration of the visual line detection device 80 according to the modification example of the embodiment has been described with reference to FIG. 8. In the modification example, as described above, the display surface 811 of the display unit 810 is observed through at least one optical member (for example, the optical path changing element 841, the lens 820, and the light guide member 830) by the user 800. Then, the light is radiated to the eyeball of the user 800 observing the display surface 811 by the light source 850 and the reflected light of the radiated light from the eyeball is detected by the imaging unit 842, so that the captured image of the eyeball is acquired.

Here, as indicated by the dotted-line arrow and the dashed-line arrow in FIG. 8, in the modification example, an optical path (first optical path) along which the light from the display surface 811 of the display unit 810 travels from the display surface 811 to the eyeball of the user 800 and an optical path (second optical path) along which the reflected light from the eyeball of the user 800, which is reflected light of the light radiated from the light source 850, travels from the eyeball to the imaging unit 842 pass the same optical members. Thus, in the modification example, the reflected light from the eyeball passes through the optical members installed in the first optical path and is incident on the imaging unit 842. Accordingly, in the visual line detection device 80 according to the modification example, it is possible to obtain the advantage of further improving the precision of the visual line detection, as in the visual line detection device 10.

[4-3. Application to Head-Mounted Display]

Next, another modification example in which the visual line detection process according to the embodiment is applied to another device other than an imaging device will be described. The visual line detection process according to the embodiment can be applied to, for example, a head-mounted display (HMD) device.

Figure 9A:
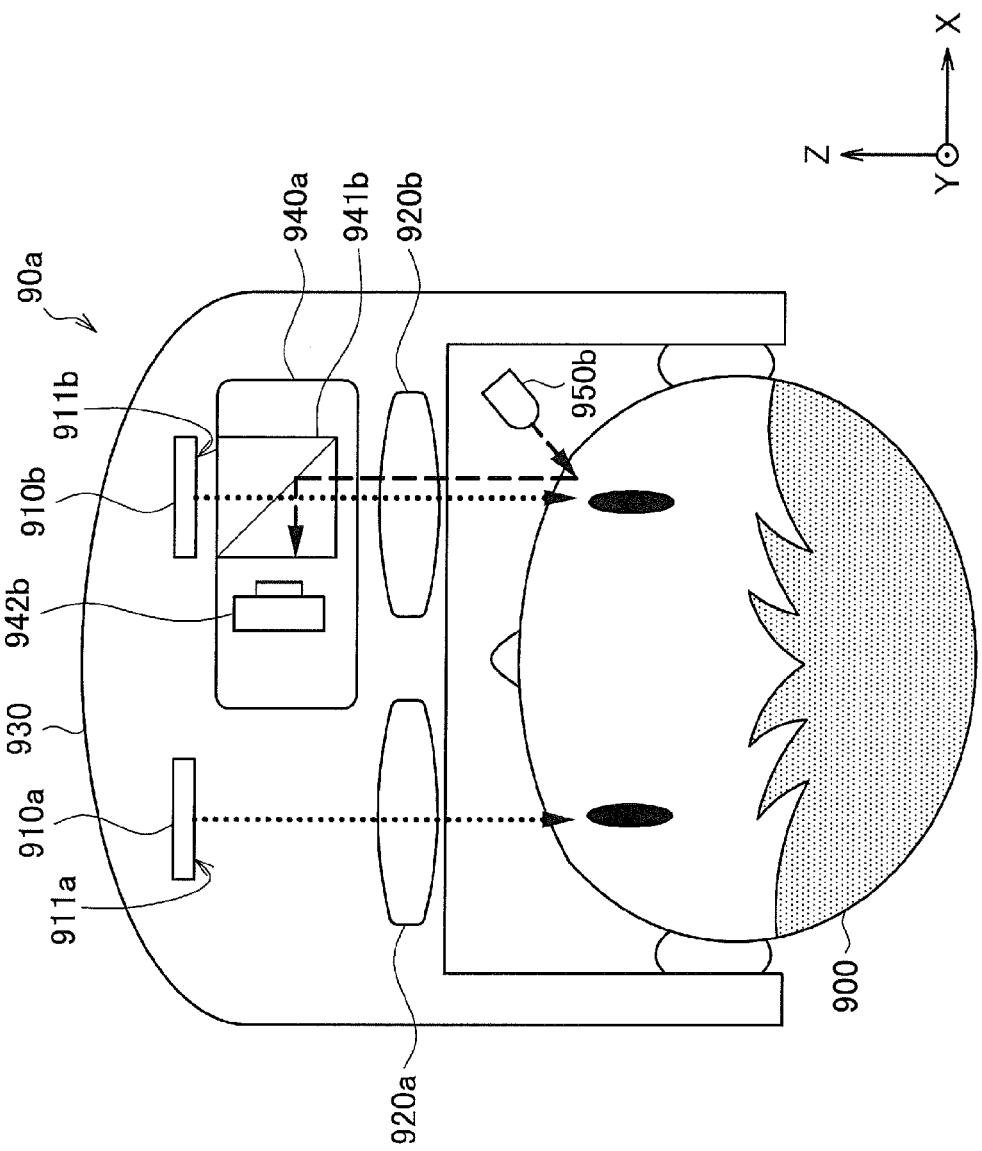
FIG. 9A is a schematic diagram illustrating an example of the configuration of a head-mounted display to which the visual line detection process according to the embodiment is applied.
Figure 9B:
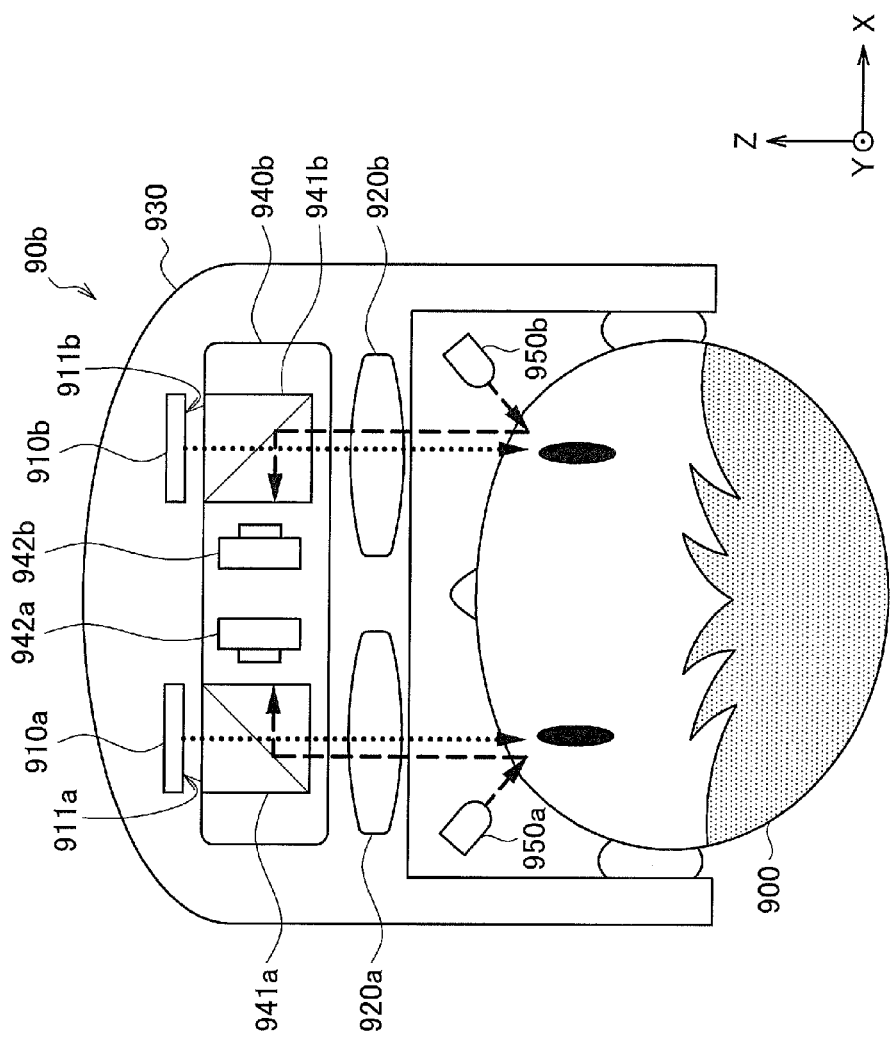
FIG. 9B is a schematic diagram illustrating an example of the configuration of a head-mounted display to which the visual line detection process according to the embodiment is applied.
Figure 9C:
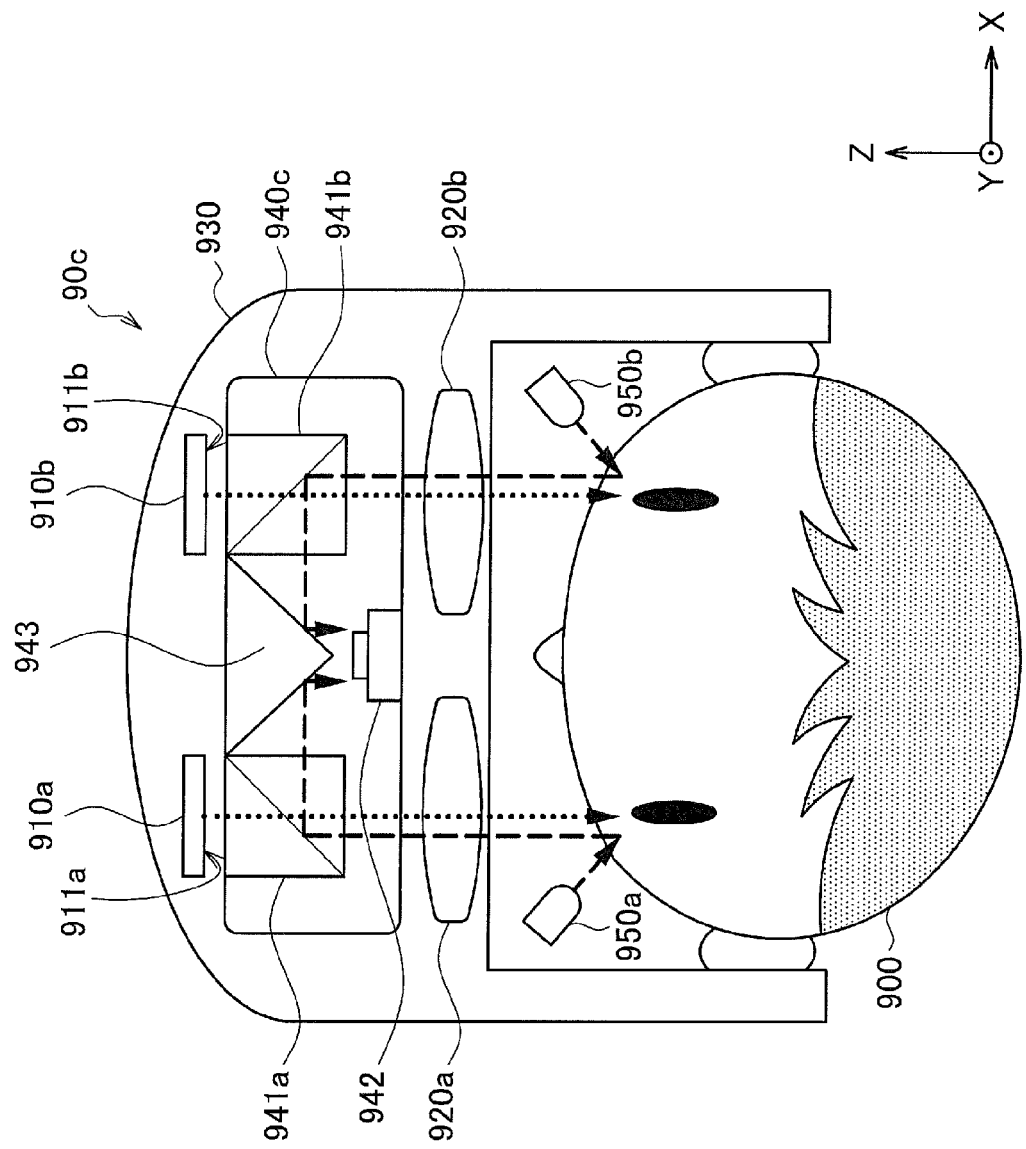
FIG. 9C is a schematic diagram illustrating an example of the configuration of a head-mounted display to which the visual line detection process according to the embodiment is applied.

An overall configuration of a head-mounted display device to which the visual line detection process according to the embodiment is applied will be described with reference to FIGS. 9A to 9C. FIGS. 9A to 9C are schematic diagrams illustrating one example of the configuration of the head-mounted display device to which the visual line detection process according to the embodiment is applied. In the description of the modification example, the visual line detection device according to the embodiment refers to a head-mounted display device to which the visual line detection process according to the embodiment is applied unless otherwise mentioned.

Referring to FIGS. 9A to 9C, visual line detection devices 90a, 90b, and 90c are each the head-mounted display device to which the visual line detection process according to the embodiment is applied and have partially different configurations. In FIGS. 9A to 9C, a user 900 wearing the visual line detection devices 90a, 90b, and 90c is illustrated along with the visual line detection devices 90a, 90b, and 90c. An optical path of light between the eyeball of the user 900 and each of the visual line detection devices 90a, 90b, and 90c within the visual line detection devices 90a, 90b, and 90c is indicated by an arrow. FIGS. 9A to 9C schematically illustrate cases in which the user 900 wearing the visual line detection devices 90a, 90b, and 90c is viewed from above. In the following description of the modification example, as illustrated in FIGS. 9A to 9C, a direction in which the user 900 faces is defined as a Z-axis direction. When viewed by the user 900, the horizontal direction is defined as an X-axis direction and the vertical direction is defined as a Y-axis direction. A direction of the Z axis in which the user views is defined as a positive direction of the Z axis, and the right side of the X axis when viewed by the user is defined as a positive direction of the X axis.

Hereinafter, the configurations of the visual line detection devices 90a, 90b, and 90c according to the modification example will be each described in order with reference to FIGS. 9A to 9C.

Referring to FIG. 9A, the visual line detection device 90a is a head-mounted display device and includes display units 910a and 910b, lenses 920a and 920b, a casing 930, a visual line detection unit 940a, and a light source 950a.

The display units 910a and 910b correspond to the display unit 110 of the visual line detection device 10 illustrated in FIGS. 1 and 2A. The display units 910a and 910b are arranged at positions at which display surfaces 911a and 911b face the left and right eyeballs of the user 900 in the negative direction of the Z axis. Any content can be displayed on the display surfaces 911a and 911b of the display units 910a and 910b. The user 900 observes various kinds of content displayed on the display surfaces 911a and 911b by observing the display surfaces 911a and 911b of the display units 910a and 910b arranged in front of the eyes of the user.

The lenses 920a and 920b are optical members that have a function of expanding display of the content on the display surfaces 911a and 911b of the display units 910a and 910b at predetermined magnification. The lenses 920a and 920b correspond to the magnifier unit 130 of the visual line detection device 10 illustrated in FIGS. 1 and 2A. As illustrated in FIG. 9A, the lenses 920a and 920b are arranged in front of the left and right eyeballs of the user 900, respectively, and expand the display of the content on the display surfaces 911a and 911b. In the example illustrated in FIG. 9A, the single lens is illustrated as each of the lenses 920a and 920b. However, in the visual line detection device 90a, a lens system in which a plurality of various lenses are combined and appropriately adjusted to expand and display the content at predetermined magnification may be each installed instead of the lenses 920a and 920b.

The casing 930 is, for example, a casing of the head-mounted display device and is a glasses-type casing mounted on the user 900. The display units 910a and 910b, the lenses 920a and 920b, and the visual line detection unit 940a are arranged at predetermined positions inside the casing 930.

The visual line detection device 90a performs a visual line detection process on one eyeball of the user 900. In the example illustrated in FIG. 9A, the visual line detection device 90a has a configuration to perform a visual line detection process on the right eyeball of the user 900. The visual line detection device 90a includes a visual line detection unit 940a between the display unit 910b and the lens 920b corresponding to the right eyeball of the user 900. As illustrated in FIG. 9A, in the visual line detection device 90a, light from the display surface 911a of the display unit 910a passes through the lens 920a in the negative direction of the Z axis and is incident on the left eyeball of the user 900. Light from the display surface 911b of the display unit 910b sequentially passes through the visual line detection unit 940a and the lens 920b in the negative direction of the Z axis and is incident on the right eyeball of the user 900. In FIG. 9A, optical paths of the light from the display surfaces 911a and 911b are indicated by dotted-line arrows.

The visual line detection unit 940a includes an optical path changing element 941b and an imaging unit 942b. The light from the display surface 911b of the display unit 910b is linearly transmitted through the optical path changing element 941b in the negative direction of the Z axis, is incident on the lens 920b, and arrives at the right eyeball of the user. The optical path changing element 941b of the imaging unit 942b corresponds to the optical path changing element 120 and the imaging unit 160 of the visual line detection device 10 illustrated in FIGS. 1 and 2A. The optical path changing element 941b has the same function and configuration as the optical path changing element 120 and is an optical member that has a mirror function of linearly transmitting light incident in one direction and reflecting light (or a part of the light) coming from another direction in a predetermined direction. Specifically, the optical path changing element 941b is, for example, a beam splitter, and transmits light incident in the positive direction of the Z axis while maintaining a traveling direction of the light and reflects light incident in the negative direction of the Z axis in the negative direction of the X axis. The imaging unit 942b is installed in the negative direction of the X axis to be adjacent to the optical path changing element 941b so that a light reception surface faces the optical path changing element 941b.

The light source 950b radiates light to the right eyeball of the user observing the display surface 911b of the display unit 910b. For example, the light source 950b may be an LED and may radiate infrared light. The light source 950b corresponds to the LEDs 141 to 148 which are the light sources of the visual line detection device 10 illustrated in FIG. 2B. In the example illustrated in FIG. 9A, the single light source 950b is illustrated. However, the visual line detection device 90a may include a plurality of light sources that radiate light to an eyeball of the user 900 from different directions, as in the visual line detection device 10. The light source 950b may be fixed in a partial region of the casing 930 by a supporting member (not illustrated).

Reflected light from the right eyeball of the user 900, which is reflected light of the light radiated from the light source 950b, follows an optical path which the light from the display surface 911b of the display unit 910b follows in a reverse direction and arrives at the optical path changing element 941b. That is, the reflected light from the right eyeball of the user 900 passes through the lens 920b and arrives at the optical path changing element 941b. As described above, since the optical path changing element 941b has the function of reflecting the light incident in the negative direction of the Z axis in the negative direction of the X axis, the optical path of the reflected light is changed by the optical path changing element 941b and the reflected light is incident on the imaging unit 942b. Thus, the imaging unit 942b detects the reflected light from the right eyeball of the user 900 and acquires a captured image of the right eyeball of the user 900. In FIG. 9A, an optical path along which the light radiated from the light source 950b is reflected from the right eyeball of the user 900 and arrives at the imaging unit 942b is indicated by a dashed line arrow.

FIG. 9B is a diagram illustrating an overall configuration of the head-mounted display device which has a different configuration from the visual line detection device 90a illustrated in FIG. 9A and to which the visual line detection process according to the embodiment is applied. Referring to FIG. 9B, the visual line detection device 90b includes display units 910a and 910b, lenses 920a and 920b, a casing 930, a visual line detection unit 940b, and light sources 950a and 950b.

Here, the visual line detection device 90b illustrated in FIG. 9B corresponds to a device in which the visual line detection unit 940a is changed to the visual line detection unit 940b and the light source 950a is added to the visual line detection device 90a illustrated in FIG. 9A. Accordingly, in the description of the visual line detection device 90b, the visual line detection unit 940b and the light source 950a will be mainly described and the detailed description of the remaining configuration will be omitted.

The visual line detection device 90b performs a visual line detection process on both of the eyeballs of the user 900. Accordingly, the visual line detection device 90b includes the visual line detection unit 940b between the display units 910a and 910b and the lenses 920a and 920b corresponding to the left and right eyeballs of the user 900. As illustrated in FIG. 9B, in the visual line detection device 90b, light from the display surface 911a of the display unit 910a sequentially passes through the visual line detection unit 940b and the lens 920a in the negative direction of the Z axis and is incident on the left eyeball of the user 900. Also, light from the display surface 911b of the display unit 910b sequentially passes through the visual line detection unit 940b and the lens 920b in the negative direction of the Z axis and is incident on the right eyeball of the user 900. In FIG. 9B, optical paths of the light from the display surfaces 911a and 911b are indicated by dotted-line arrows.

The visual line detection unit 940b includes optical path changing elements 941a and 941b and imaging units 942a and 942b. The optical path changing elements 941a and 941b and the imaging units 942a and 942b correspond to the optical path changing element 120 and the imaging unit 160 of the visual line detection device 10 illustrated in FIGS. 1 and 2A.

Here, the visual line detection unit 940b has a configuration in which the optical path changing element 941a and the imaging unit 942a corresponding to the left eyeball of the user 900 are added to the visual line detection unit 940a illustrated in FIG. 9A. Specifically, in the visual line detection unit 940b, the optical path changing element 941b is installed between the display surface 911b of the display unit 910b and the lens 920b and the optical path changing element 941a is installed between the display surface 911a of the display unit 910a and the lens 920a. Accordingly, the light from the display surface 911b of the display unit 910b is linearly transmitted through the optical path changing element 941b in the negative direction of the Z axis, is incident on the lens 920b, and arrives at the right eyeball of the user. Also, the light from the display surface 911a of the display unit 910a linearly passes through the optical path changing element 941a in the negative direction of the Z axis, is incident on the lens 920a, and arrives at the left eyeball of the user. The optical path changing elements 941a and 941b have the same function and configuration as the optical path changing element 120 and are optical members that have a mirror function of linearly transmitting light incident in one direction and reflecting light (or a part of the light) coming from another direction in a predetermined direction. Specifically, the optical path changing element 941a transmits light incident in the positive direction of the Z axis while maintaining a traveling direction of the light and reflects light incident in the negative direction of the Z axis in the positive direction of the X axis. Also, the optical path changing element 941b transmits light incident in the positive direction of the Z axis while maintaining a traveling direction of the light and reflects light incident in the negative direction of the Z axis in the negative direction of the X axis.

In the visual line detection device 90b, the light source 950a is added to the visual line detection device 90a illustrated in FIG. 9A. The light source 950a radiates light to the left eyeball of the user observing the display surface 911a of the display unit 910a. For example, the light source 950a may be an LED and may radiate infrared light. The light source 950a corresponds to the LEDs 141 to 148 which are the light sources of the visual line detection device 10 illustrated in FIG. 2B. The light source 950b may be fixed in a partial region of the casing 930 by a supporting member (not illustrated). In the example illustrated in FIG. 9B, the light sources 950a and 950b are illustrated separately for the left and right eyeballs. However, the visual line detection device 90b may include a plurality of light sources that radiate light to the left and right eyeballs of the user 900 from different directions, as in the visual line detection device 10.

Reflected light from the left eyeball of the user 900, which is reflected light of the light radiated from the light source 950a, follows an optical path which the light from the display surface 911a of the display unit 910a follows in a reverse direction and arrives at the optical path changing element 941a. Then, the optical path of the reflected light is changed in the positive direction of the X axis by the optical path changing element 941a and the reflected light is incident on the imaging unit 942a. Also, reflected light from the right eyeball of the user 900, which is reflected light of the light radiated from the light source 950b, follows an optical path which the light from the display surface 911b of the display unit 910b follows in a reverse direction and arrives at the optical path changing element 941b. Then, the optical path of the reflected light is changed in the negative direction of the X axis by the optical path changing element 941b and the reflected light is incident on the imaging unit 942b. Thus, in the visual line detection device 90b, the light from the light sources 950a and 950b is radiated to the left and right eyeballs of the user and the imaging units 942a and 942b detect the reflected light from the left and right eyeballs, respectively, so that the captured images of the left and right eyeballs are acquired. In FIG. 9B, optical paths along which the light radiated from the light sources 950a and 950b is reflected from the left and right eyeballs of the user 900 and arrives at the imaging units 942a and 942b are indicated by dashed line arrows.

FIG. 9C is a diagram illustrating an overall configuration of the head-mounted display device which has a different configuration from the visual line detection devices 90a and 90b illustrated in FIGS. 9A and 9B and to which the visual line detection process according to the embodiment is applied. Referring to FIG. 9C, the visual line detection device 90c includes display units 910a and 910b, lenses 920a and 920b, a casing 930 a visual line detection unit 940c, and light sources 950a and 950b.

Here, the visual line detection device 90c illustrated in FIG. 9C corresponds to a device in which the visual line detection unit 940b is changed to the visual line detection unit 940c compared to the visual line detection device 90b illustrated in FIG. 9B. Accordingly, in the description of the visual line detection device 90c, the configuration of the visual line detection unit 940c will be mainly described and the detailed description of the remaining configuration will be omitted.

The visual line detection unit 940c includes optical path changing elements 941a, 941b, and 943 and an imaging unit 942. The optical path changing elements 941a and 941b and the imaging unit 942 correspond to the optical path changing element 120 and the imaging unit 160 of the visual line detection device 10 illustrated in FIGS. 1 and 2A.

Here, the visual line detection unit 940c illustrated in FIG. 9C corresponds to a unit in which the optical path changing element 943 is further added to the visual line detection unit 940b illustrated in FIG. 9B and the imaging units 942a and 942b are replaced with the imaging unit 942. The functions and configurations of the optical path changing elements 941a and 941b of the visual line detection unit 940c are the same as the functions and configurations of the optical path changing elements 941a and 941b of the visual line detection unit 940b. Accordingly, in the visual line detection device 90c, the light from the display surface 911b of the display unit 910b is linearly transmitted through the optical path changing element 941b in the negative direction of the Z axis, is incident on the lens 920b, and arrives at the right eyeball of the user. Also, the light from the display surface 911a of the display unit 910a is linearly transmitted through the optical path changing element 941a in the negative direction of the Z axis, is incident on the lens 920a, and arrives at the left eyeball of the user. In FIG. 9C, optical paths of the light from the display surfaces 911a and 911b are indicated by dotted-line arrows.

In the visual line detection unit 940c, the optical path changing element 943 is installed between the optical path changing elements 941a and 941b. The optical path changing element 943 has a function of reflecting light incident from the optical path changing elements 941a and 942b in the negative direction of the Z axis. The imaging unit 942 is arranged in the negative direction of the Z axis of the optical path changing element 943 so that a light reception surface faces in the positive direction of the Z axis. Accordingly, reflected light from the left eyeball of the user 900, which is reflected light of the light radiated from the light source 950a, follows an optical path which the light from the display surface 911a of the display unit 910a follows in a reverse direction and arrives at the optical path changing element 941a. Then, the optical path of the reflected light is changed in the positive direction of the X axis by the optical path changing element 941a, the optical path of the reflected light is further changed in the negative direction of the Z axis by the optical path changing element 943, and the reflected light is incident on the imaging unit 942a. Also, reflected light from the right eyeball of the user 900, which is reflected light of the light radiated from the light source 950b, follows an optical path which the light from the display surface 911b of the display unit 910b follows in a reverse direction and arrives at the optical path changing element 941b. Then, the optical path of the reflected light is changed in the negative direction of the X axis by the optical path changing element 941b, the optical path of the reflected light is further changed in the negative direction of the Z axis by the optical path changing element 943, and the reflected light is incident on the imaging unit 942b. Thus, in the visual line detection device 90c, the reflected light from the left and right eyeballs is detected by the single imaging unit 942, instead of the user and the imaging units 942a and 942b installed for the left and right eyeballs in the visual line detection device 90b, so that the captured images of the left and right eyeballs are acquired. In FIG. 9C, optical paths along which the light radiated from the light sources 950a and 950b is reflected from the left and right eyeballs of the user 900 and arrives at the imaging unit 942 are indicated by dashed line arrows.

As described above, the visual line detection devices 90a, 90b, and 90c acquire the captured image of the eyeball of the user by detecting the reflected light from the eyeball of the user in the head-mounted display device. Then, the visual line detection devices 90a, 90b, and 90c perform the visual line detection process for the user 900 on the display surfaces 911a and 911b of the display units 910a and 910b based on the captured image as in the visual line detection device 10. As the visual line detection process of the visual line detection devices 90a, 90b, and 90c, the same process as the visual line detection process of the visual line detection device 10 described in the foregoing <3. Details of visual line detection process> may be performed.

The overall configurations of the visual line detection devices 90a, 90b, and 90c according to the modification example of the embodiment have been described with reference to FIGS. 9A to 9C. In the modification example, as described above, the display surfaces 911a and 911b of the display units 910a and 910b are observed through at least one optical member (for example, the optical path changing elements 941a and 941b and the lenses 920a and 920b) by the user 900. Then, the light is radiated to the eyeball of the user 900 observing the display surfaces 911a and 911b by the light sources 950a and 950b and the reflected light of the light radiated from the eyeballs is detected by the imaging units 942, 942a, and 942b, so that the captured image of the eyeball is acquired.

Here, as indicated by the dotted-line arrow and the dashed-line arrow in FIGS. 9A to 9C, in the modification example, the reflected light from the eyeball of the user 900, which is reflected light of the light radiated from the light sources 950a and 950b, passes through the optical members installed in the optical path along which the light from the display surfaces 911a and 911b of the display units 910a and 910b travels from the display surfaces 911a and 911b to the eyeball of the user 900, and is incident on the imaging units 942, 942a, and 942b. Accordingly, in the visual line detection devices 90a, 90b, and 90c according to the modification example, it is possible to obtain the advantage of further improving the precision of the visual line detection, as in the visual line detection devices 10 and 80.

In the modification example, as in the visual line detection devices 90b and 90c illustrated in FIGS. 9B and 9C, light may be radiated from the light sources 950a and 950b to the left and right eyeballs of the user and reflected light from the left and right eyeballs is detected by the imaging units 942a and 942b, so that captured images of the left and right eyeballs can be acquired, respectively. Then, the visual line detection process may be performed on each of the left and right eyeballs. Thus, by performing the visual line detection process on each of the left and right eyeballs, it is possible to further improve the precision of the visual line detection. Also, by performing the visual line vector calculation process on each of the left and right eyeballs, for example, it is possible to further acquire information such as parallax information.

In the modification example, as in the visual line detection device 90c illustrated in FIG. 9C, the configuration of the visual line detection unit 940c can be simplified more than the visual line detection unit 940b of the visual line detection device 90b illustrated in FIG. 9B. Accordingly, with the more simplified configuration, it is possible to perform the visual line detection process with the same precision as that of the visual line detection device 90b.

The visual line of the user detected in the visual line detection devices 80, 90a, 90b, and 90c may be used in various operations of the glasses-type wearable device and the head-mounted display device which are the visual line detection devices 80, 90a, 90b, and 90c. For example, the detected visual line of the user may be used as an input unit that performs various operation inputs from the user on the glasses-type wearable device and the head-mounted display device. Specifically, by detecting a visual line in any one of the upper, lower, right, and left end regions of the display surfaces 811, 911a, and 911b, content displayed on the display surfaces 811, 911a, 911b may be scrolled and displayed in a direction in which the visual line is detected. Also, by displaying icons corresponding to various operations performed by the glasses-type wearable device and the head-mounted display device on the display surfaces 811, 911a, and 911b and continuously detecting a visual line of the user on the icons for a predetermined time, operations corresponding to the icons may be performed. The operations corresponding to the icons may be, for example, various operations performed in information processing devices such as general PCs, such as turning OFF power (shutdown) of the glasses-type wearable device and the head-mounted display device or activation of various applications. The detected visual line of the user may be used as a pointing device moving a pointer displayed on the display surfaces 811, 911a, and 911b. For example, the pointer may be moved on the display surfaces 811, 911a, and 911b according to a change in the detected visual line of the user.

5. Processing Order of Visual Line Detection Method

Figure 10:
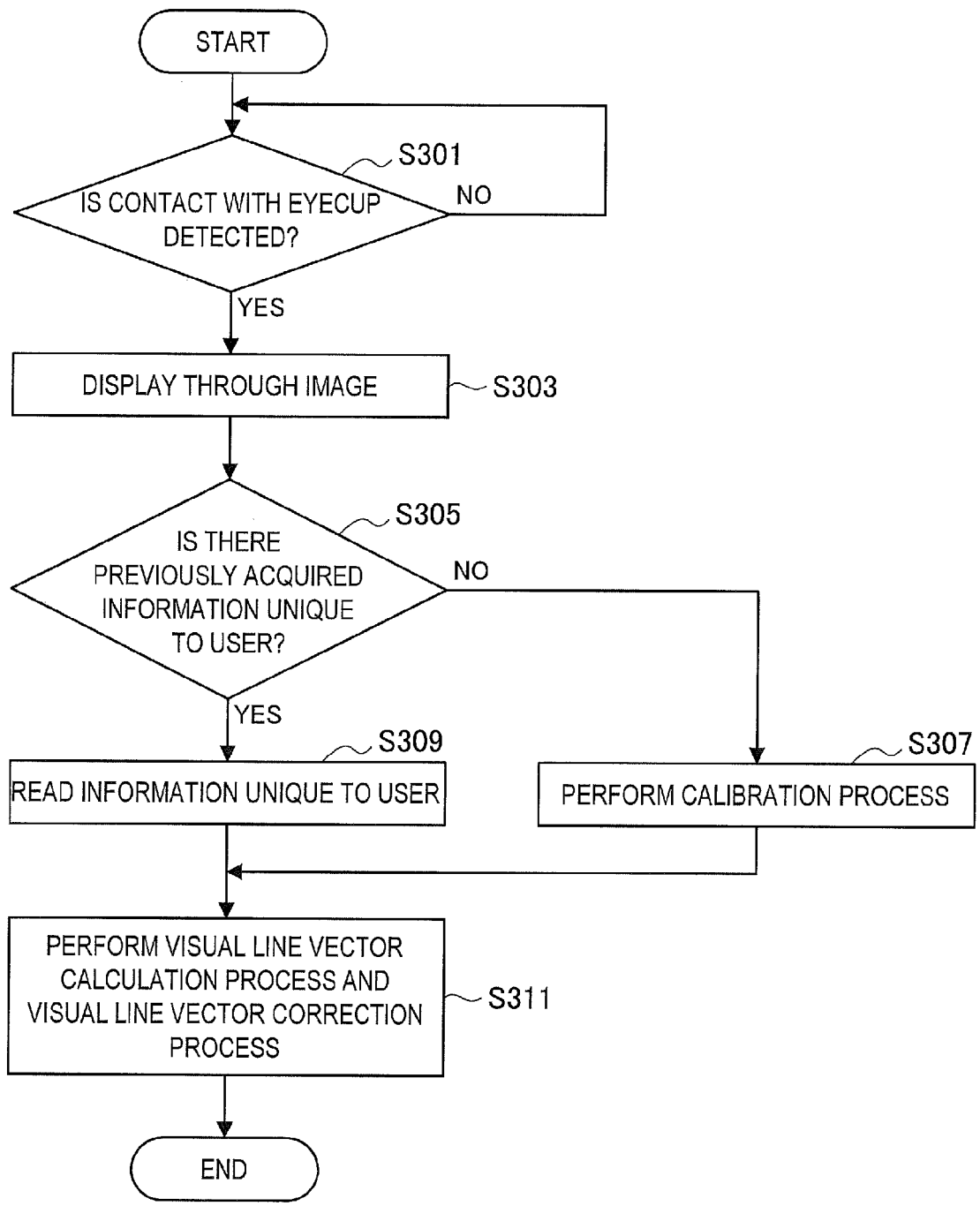
FIG. 10 is a flowchart illustrating a processing order of a visual line detection method according to an embodiment of the present disclosure.

Next, a processing order of a visual line detection method according to an embodiment of the present disclosure will be described with reference to FIG. 10. FIG. 10 is a flowchart illustrating the processing order of the visual line detection method according to the embodiment of the present disclosure. In the following description of the processing order of the visual line detection method according to the embodiment, a case in which the visual line detection device 10 is an EVF connected to an imaging device will be described. Steps of the flowchart in FIG. 10 may be performed by the constituent elements of the visual line detection device 10 and the imaging device 20 illustrated in FIGS. 1, 2A, 2B, and 3. However, in the following description, detailed description of the functions and the configurations of the constituent elements will be omitted.

Referring to FIG. 10, first, it is determined in step S301 whether contact of an eye of the user with the eyecup 150 is detected. The contact of an eye of the user with the eyecup 150 may be detected by, for example, a contact sensor installed in the eyecup 150. When the contact of an eye of the user is detected in step S301, the user is considered to be looking into the visual line detection device 10. Therefore, the process proceeds to step S303 and a through image which is content is displayed on the display surface 111 of the display unit 110. When the contact of an eye of the user is not detected in step S301, the user is considered not to be using the visual line detection device 10. Therefore, nothing is displayed on the display surface 111 of the display unit 110 and this state is maintained until the contact of an eye of the user with the eyecup 150 is detected.

In the embodiment, the processes of step S301 and step S303 may not be performed. When the processes of step S301 and step S303 are not performed, content may be displayed normally on the display surface 111 of the display unit 110 of the visual line detection device 10. However, by selectively driving the display unit 110 according to a use status of the visual line detection device 10, as described in step S301 and step S303, it is possible to reduce power consumption.

When the through image is displayed on the display surface 111 of the display unit 110 in step S303, whether there is previously acquired information that is unique to the user is subsequently determined for the user attempting to use the visual line detection device 10 in step S305. Here, the information unique to the user may be information such as the observation state information used in the visual line detection process according to the embodiment, the driving condition of the light source, or the eyeball information described in the foregoing <3. Details of visual line detection process>. After the information unique to the user is acquired once, the information unique to the user is stored in a storage unit installed in the visual line detection device 10 or the imaging device 20 in association with the user. In step S305, a user attempting to use the visual line detection device 10 is specified and it is determined whether the unique information associated with the specified user is stored in the storage unit. In the process of specifying the user attempting to use the visual line detection device 10, for example, the visual line detection device 10 or the imaging device 20 may have a user registration function and a user selection function. By manually selecting a user by the user registration function and the user selection function, the user may be specified. In the process of specifying a user attempting to use the visual line detection device 10, the visual line detection device 10 or the imaging device 20 may have various biometric authentication functions such as iris authentication, vein authentication, and fingerprint authentication. By automatically performing personal authentication or individual identification of the user by the biometric authentication functions, the user may be specified.

When it is determined in step S305 that there is no unique information for the user attempting to use the visual line detection device 10, the process proceeds to step S307 and the calibration process is performed for the user. In the calibration process of step S307, for example, each process described in the foregoing [3-3. Calibration process] is performed and the information unique to the user to be used in the visual line detection process is acquired. When the calibration process ends, the process proceeds to step S311.

Conversely, when it is determined in step S305 that there is the unique information for the user attempting to use the visual line detection device 10, the process proceeds to step S309 and the corresponding information that is unique to the user is read from the storage unit in which the information unique to the user is stored. When the information unique to the user is read from the storage unit, the process proceeds to step S311.

In step S311, the process of calculating the visual line vector of the user on the display surface 111 of the display unit 110 and the visual line vector correction process are performed using the information unique to the user that was acquired in step S307 and the information unique to the user that was read in step S309. In the visual line vector calculation process and the visual line vector correction process in step S311, for example, each process described in the foregoing [3-1. Visual line vector calculation process], [3-2. Light source driving control], and [3-3. Calibration process] is performed. The observation state information used in the visual line vector calculation process, the driving condition of the light source based on the observation state information, or the like may be acquired separately prior to the series of the processes illustrated in FIG. 10 and may be stored in the storage unit, and may be read in step S309, or may be acquired separately at any timing during the series of processes illustrated in FIG. 10. For example, the observation state information, the driving condition, or the like may be acquired together with the calibration process in step S307.

The processing order of the visual line detection method according to the embodiment has been described above. As described above, the visual line detection method according to the above-described embodiment may be performed by each constituent element of the visual line detection device 10 and the imaging device 20 illustrated in FIGS. 1, 2A, 2B, and 3. Accordingly, in the visual line vector calculation process shown in step S311, the light from the display surface 111 of the display unit 110 follows the first optical path that passes at least one optical member and is incident on an eyeball of the user. Then, the light is radiated to the eyeball of the user observing the display surface 111 and the reflected light of the radiated light from the eyeball of the user is detected, so that the captured image of the eyeball used to detect a visual line of the user on the display surface 111 is acquired. The reflected light of the radiated light from the eyeball follows the second optical path that passes at least the optical members installed in the first optical path and is incident on the imaging unit. Thus, according to the embodiment, the precision of the visual line detection is further improved.

6. Conclusion

In the embodiment, as described above, the light is radiated to the eyeball of the user observing the display surface through at least one optical member. Then, when the reflected light of the radiated light from the eyeball of the user is detected, the captured image of the eyeball used to detect the visual line of the user on the display surface is acquired. The reflected light of the radiated light from the eyeball of the user follows the second optical path, which passes at least the optical member installed in the first optical path along which the light from the display surface travels from the display surface to the eyeball of the user, to be detected. Then, based on the captured image of the eyeball of the user acquired in this way, the visual line of the user on the display surface is detected. In the embodiment, with the foregoing configuration, the first and second optical paths include almost the same optical members, and thus are optically similar optical paths. Accordingly, the precision of the visual line detection is further improved.

In the embodiment, the plurality of light sources are arranged so that the light is radiated to the eyeball of the user in a plurality of different directions. Further, the plurality of light sources can be selectively driven according to the driving condition unique to the user. Accordingly, since the light suitable for statuses of the user, such as the shape of an eye of the user, whether the user wears glasses, and a direction in which the user observes the display surface, can be radiated, the precision of the visual line detection is further improved.

In the embodiment, by performing the calibration process of acquiring the eyeball information used to correct an error caused due to the shape or the size of an eye of the user and correcting the visual line vector based on the eyeball information, the visual line of the user is detected. Accordingly, the visual line detection is realized with higher precision.

The preferred embodiments of the present disclosure have been described in detail above with reference to the appended drawings, but the technical scope of the present disclosure is not limited thereto. It should be apparent to those skilled in the art that various modifications and corrections can be made within the scope of the technical spirit described in the claims, and the modifications and the corrections are, of course, construed to pertain to the technical scope of the present disclosure.

For example, the configuration in which the display surface 111 of the display unit 110 and the eyeball 500 of the user are located on the same straight line has been described above, as illustrated in FIGS. 1, 2A, 2B, and 7, but embodiments of the present disclosure are not limited to the embodiment. For example, the display surface 111 and the eyeball 500 of the user may not be located on the same straight line. An optical member changing an optical path, such as a mirror or a prism, may be appropriately installed between the display surface 111 and the eyeball 500 of the user so that the light from the display surface 111 is guided to the eyeball 500 of the user. Thus, in the embodiment, a positional relation between the display surface 111 and the eyeball 500 of the user in the visual line detection device 10 is not limited to the specific positional relation, as illustrated in FIGS. 1, 2A, 2B, and 7. Accordingly, since a degree of design freedom of the arrangement of the constituent elements in the visual line detection device 10 is added, for example, it is possible to realize the configuration of the visual line detection device 10 having a small size and excellent portability.

The imaging device, the glasses-type wearable device, and the head-mounted display device have been described above as the devices to which the visual line detection process according to the embodiment is applied, but the embodiment is not limited to these examples. The visual line detection process according to the embodiment can be applied to another apparatus or device as long as the apparatus or device has a configuration in which at least one optical member is installed between the display surface 111 on which various kinds of content are displayed and the eyeball 500 of the user. In such an apparatus or device, by appropriately providing a light source that radiates light to the eyeball 500 of the user and an imaging unit that detects reflected light of the radiated light from the eyeball 500 and acquires a captured image of the eyeball 500 so that a relation between the above-described first and second optical paths is maintained, the visual line detection process according to the embodiment can be applied.

Additionally, the present technology may also be configured as below:

(1) A visual line detection device including:
at least one light source configured to radiate light to an eyeball of a user observing a display surface through at least one optical member; and
an imaging unit configured to acquire a captured image of the eyeball used to detect a visual line of the user on the display surface by detecting reflected light of the light from the eyeball,
wherein the reflected right from the eyeball passes through at least the optical member installed in an optical path along which the light from the display surface travels from the display surface to the eyeball of the user, and is incident on the imaging unit.

(2) The visual line detection device according to (1), wherein a plurality of the light sources are installed at positions at which the light is radiated to the eyeball of the user in mutually different directions.

(3) The visual line detection device according to (2), wherein the plurality of light sources are selectively driven under a driving condition according to observation state information regarding a state in which the user observes the display surface.

(4) The visual line detection device according to (3), wherein the observation state information includes at least one of information regarding a shape of an eye of the user, information regarding whether the user wears glasses, and information regarding a direction in which the user observes the display surface.

(5) The visual line detection device according to any one of (2) to (4), wherein the plurality of light sources radiate the light in a vertical direction or a horizontal direction with respect to the eyeball of the user.

(6) The visual line detection device according to any one of (2) to (4), wherein the plurality of light sources radiate the light in four mutually different directions with respect to the eyeball of the user.

(7) The visual line detection device according to any one of (1) to (6), wherein the visual line of the user on the display surface is detected by calculating a visual line vector indicating a direction of the eyeball of the user based on an image of a pupil contained in the captured image of the eyeball acquired by the imaging unit and a Purkinje image.

(8) The visual line detection device according to (7), wherein the visual line of the user on the display surface is detected by performing a correction process on the visual line vector based on eyeball information regarding the eyeball of the user including at least a correlation between the visual line vector and a direction in which the user views the display surface.

(9) The visual line detection device according to (8),
wherein the eyeball information is acquired through a calibration process performed for each user, and
wherein the eyeball information corresponding to the user observing the display surface is read according to this user and the read eyeball information is used in the correction process.

(10) The visual line detection device according to (9), wherein an authentication process of the user is performed based on an iris of the eyeball of the user contained in the captured image acquired by the imaging unit and the eyeball information corresponding to this user is read based on a result of the authentication process.

(11) The visual line detection device according to any one of (1) to (10), wherein the optical member installed in the optical path along which the light from the display surface travels from the display surface to the eyeball of the user includes a magnifier unit configured to expand and display content displayed on the display surface for the user.

(12) The visual line detection device according to any one of (1) to (11), further including:
an eyecup configured to come into contact with an eye of the user when the user observes the display surface,
wherein content is displayed on the display surface when the contact of the eyecup with the eye of the user is detected.

(13) The visual line detection device according to any one of (1) to (12),
wherein the light source radiates light with an infrared band to the eyeball of the user, and
wherein an infrared-light passing mechanism shielding light with a wavelength band other than the infrared band is installed on a front stage of the imaging unit in an optical path along which the reflected light from the eyeball travels from the eyeball to the imaging unit.

(14) The visual line detection device according to any one of (1) to (13), further including:
a visual line detection processing unit configured to calculate a visual line vector indicating a direction of the eyeball of the user based on an image of a pupil contained in the captured image of the eyeball acquired by the imaging unit and a Purkinje image; and
a calibration processing unit configured to acquire eyeball information which is information regarding the eyeball of the user including at least a correlation between the visual line vector and a direction in which the user views the display surface,
wherein the visual line detection processing unit detects the visual line of the user on the display surface by performing a correction process on the visual line vector based on the eyeball information.

(15) The visual line detection device according to any one of (1) to (14),
wherein the visual line detection device is an electronic view finder connected to an imaging device acquiring a captured image of a photographing target, and
wherein a through image in which the photographing target acquired by an image sensor included in the imaging device is shown is displayed on the display surface.

(16) The visual line detection device according to any one of (1) to (14),
wherein the visual line detection device is a glasses-type wearable device covering at least an area in front of the eyeball of the user, and
wherein given content is displayed on the display surface by a display unit included in this wearable device.

(17) The visual line detection device according to any one of (1) to (14), wherein the visual line detection device is a head-mounted display device mounted on a head of the user in a manner than the display surface is installed at a position facing the eyeball, and wherein given content is displayed on the display surface by a display unit included in this head-mounted display device.

(18) A visual line detection method including:

allowing light from a display surface to pass through at least one optical member and to be incident on an eyeball of a user;

radiating light to the eyeball of the user observing the display surface; and acquiring a captured image of the eyeball used to detect a visual line of the user on the display surface by detecting reflected light of the light from the eyeball, wherein the reflected light from the eyeball passes through at least the optical member installed in an optical path along which the light from the display surface travels from the display surface to the eyeball of the user, and is detected.

What is claimed is:

1. A visual line detection device comprising:
   a plurality of light sources configured to radiate light to an eyeball of a user observing a display surface through at least one optical member; and
   an imaging unit configured to acquire a captured image of the eyeball used to detect a visual line of the user on the display surface by detecting reflected light of the light from the eyeball,
   wherein the reflected light from the eyeball passes through at least the optical member installed in an optical path along which light from the display surface travels to the eyeball of the user, and is incident on the imaging unit, and
   wherein a driving condition of one or more of the plurality of light sources is acquired for the user by sequentially changing combinations of the plurality of light sources to be driven.

2. The visual line detection device according to claim 1, wherein the plurality of the light sources are installed at one or more positions at which the light is radiated to the eyeball of the user in mutually different directions.

3. The visual line detection device according to claim 2, wherein the plurality of light sources are selectively driven under the driving condition according to observation state information regarding a state in which the user observes the display surface.

4. The visual line detection device according to claim 3, wherein the observation state information includes at least one of information regarding a shape of an eye of the user, information regarding whether the user wears glasses, and information regarding a direction in which the user observes the display surface.

5. The visual line detection device according to claim 2, wherein the plurality of light sources radiate the light in a vertical direction or a horizontal direction with respect to the eyeball of the user.

6. The visual line detection device according to claim 2, wherein the plurality of light sources radiate the light in four mutually different directions with respect to the eyeball of the user.

7. The visual line detection device according to claim 1, wherein the visual line of the user on the display surface is detected by calculating a visual line vector indicating a direction of the eyeball of the user based on an image of a pupil contained in the captured image of the eyeball acquired by the imaging unit and a Purkinje image.

8. The visual line detection device according to claim 7, wherein the visual line of the user on the display surface is detected by performing a correction process on the visual line vector based on eyeball information regarding the eyeball of the user including at least a correlation between the visual line vector and a direction in which the user views the display surface.

9. The visual line detection device according to claim 8, wherein the eyeball information is acquired through a calibration process performed for each user, and
   wherein the eyeball information corresponding to the user observing the display surface is read according to this user and the read eyeball information is used in the correction process.

10. The visual line detection device according to claim 9, wherein an authentication process of the user is performed based on an iris of the eyeball of the user contained in the captured image acquired by the imaging unit and the eyeball information corresponding to this user is read based on a result of the authentication process.

11. The visual line detection device according to claim 1, wherein the optical member installed in the optical path along which the light from the display surface travels from the display surface to the eyeball of the user includes a magnifier unit configured to expand and display content displayed on the display surface for the user.

12. The visual line detection device according to claim 1, further comprising:
    an eyecup configured to come into contact with an eye of the user when the user observes the display surface,
    wherein content is displayed on the display surface when the contact of the eyecup with the eye of the user is detected.

13. The visual line detection device according to claim 1, wherein the plurality of light sources radiates light with an infrared band to the eyeball of the user, and
    wherein an infrared-light passing mechanism shielding light with a wavelength band other than the infrared band is installed on a front stage of the imaging unit in an optical path along which the reflected light from the eyeball travels from the eyeball to the imaging unit.

14. The visual line detection device according to claim 1, further comprising:
    a visual line detection processing unit configured to calculate a visual line vector indicating a direction of the eyeball of the user based on an image of a pupil contained in the captured image of the eyeball acquired by the imaging unit and a Purkinje image; and
    a calibration processing unit configured to acquire eyeball information which is information regarding the eyeball of the user including at least a correlation between the visual line vector and a direction in which the user views the display surface,
    wherein the visual line detection processing unit detects the visual line of the user on the display surface by performing a correction process on the visual line vector based on the eyeball information.

15. The visual line detection device according to claim 1, wherein the visual line detection device is an electronic view finder connected to an imaging device acquiring a captured image of a photographing target, and
    wherein a through image in which the photographing target acquired by an image sensor included in the imaging device is shown is displayed on the display surface.

16. The visual line detection device according to claim 1,
wherein the visual line detection device is a glasses-type wearable device covering at least an area in front of the eyeball of the user, and
wherein given content is displayed on the display surface by a display unit included in this wearable device.

17. The visual line detection device according to claim 1,
wherein the visual line detection device is a head-mounted display device mounted on a head of the user in a manner than the display surface is installed at a position facing the eyeball, and
wherein given content is displayed on the display surface by a display unit included in this head-mounted display device.

18. A visual line detection method comprising:
allowing light from a display surface to pass through at least one optical member and to be incident on an eyeball of a user;
radiating light to the eyeball of the user observing the display surface; and
acquiring a captured image of the eyeball used to detect a visual line of the user on the display surface by detecting reflected light of the light from the eyeball,
wherein the reflected light from the eyeball passes through at least the optical member installed in an optical path along which light from the display surface travels to the eyeball of the user, and is detected, and
wherein a driving condition of one or more of a plurality of light sources is acquired for the user by sequentially changing combinations of the plurality of light sources to be driven.

19. The visual line detection device according to claim 1, wherein an optical path of the reflected light is same as the optical path of the light from the display surface being observed by the user.

20. The visual line detection device according to claim 1, wherein the plurality of light sources are driven for the user based on the acquired driving condition associated with the user.

21. The visual line detection device according to claim 1, wherein the driving condition of the one or more of the plurality of light sources is acquired for the user by changing intensity of the radiated light before detection of the visual line.

22. The visual line detection device according to claim 1, further comprising a storage unit configured to store observer state information and the acquired driving condition associated with the user.

23. The visual line detection device according to claim 22, wherein the acquired driving condition associated with the user are read from the storage unit when it is determined that the observer state information corresponding to the user is stored in the storage unit.

* * * * *